(12) United States Patent
Fleischhacker et al.

(10) Patent No.: US 6,210,395 B1
(45) Date of Patent: Apr. 3, 2001

(54) HOLLOW LUMEN CABLE APPARATUS

(75) Inventors: Mark G. Fleischhacker, Minnetonka; Joseph F. Fleischhacker, Jr.; Thomas E. Hargreaves, both of Mound; Donald W. Hanson, Chanhassen, all of MN (US)

(73) Assignee: Lake Region Mfg., Inc., Chaska, MN (US)

( * ) Notice: Subject to any disclaimer, the term of this patent is extended or adjusted under 35 U.S.C. 154(b) by 0 days.

(21) Appl. No.: 08/953,059

(22) Filed: Oct. 20, 1997

Related U.S. Application Data

(62) Division of application No. 07/959,551, filed on Oct. 13, 1992, now Pat. No. 5,678,296, which is a division of application No. 07/384,393, filed on Jul. 24, 1989, now Pat. No. 5,154,705, which is a continuation-in-part of application No. 07/102,878, filed on Sep. 30, 1987, now abandoned.

(51) Int. Cl.$^7$ .................................................. A61M 25/00
(52) U.S. Cl. .......................... 604/526; 604/523; 604/524
(58) Field of Search ..................................... 604/523–526, 604/533, 264, 103.09

(56) References Cited

U.S. PATENT DOCUMENTS

| | | |
|---|---|---|
| Re. 25,543 | 3/1964 | Ruegg . |
| 267,343 | 11/1882 | Harrison . |
| 492,266 | 2/1893 | Browne . |
| 1,228,439 | 6/1917 | Hotchkiss . |
| 1,279,773 | 9/1918 | Sperling . |
| 1,429,146 | 10/1922 | Karge . |
| 1,808,193 | 6/1931 | Webb . |
| 2,048,471 | 7/1936 | Sanford . |
| 2,955,592 | 10/1960 | MacLean . |
| 3,267,697 | 8/1966 | Oldberg et al. . |
| 3,539,034 | 11/1970 | Tafeen . |
| 3,552,384 | 1/1971 | Pierie et al. . |
| 3,618,613 | 11/1971 | Schulte . |
| 3,749,085 | 7/1973 | Willson . |
| 3,749,086 | 7/1973 | Kline et al. . |
| 3,757,768 | 9/1973 | Kline . |
| 3,811,446 | 5/1974 | Lerwick et al. . |
| 3,847,140 | 11/1974 | Ayella . |
| 4,154,247 | 5/1979 | O'Neill . |
| 4,178,810 | 12/1979 | Takahashi . |
| 4,368,730 | 1/1983 | Sharrock . |
| 4,516,972 | 5/1985 | Samson . |
| 4,538,622 | 9/1985 | Samson et al. . |

(List continued on next page.)

FOREIGN PATENT DOCUMENTS

| | | |
|---|---|---|
| 3420740 A1 | 6/1984 | (DE) . |
| 0274412 | 1/1988 | (EP) . |
| 0028115 | 8/1911 | (GB) . |
| 2142944 | 6/1984 | (GB) . |

*Primary Examiner*—Sharon Kennedy
*Assistant Examiner*—Cris L. Rodriguez
(74) *Attorney, Agent, or Firm*—Michael Best & Friedrich LLP; Grady J. Frehchick

(57) ABSTRACT

A hollow lumen cable is formed by helically winding inner and outer coils with the helices of each coil being in abutting relationship and the outer coil inner diameter being less than the outer coil inner diameter being less than the outer, peripheral, diameter of the inner coil. Preferably, each coil is multifilar. After the coils are wound, an unwinding force is applied to the outer coil and the inner coil is inserted into the outer coil to have its winding inclined opposite to that of the outer coil; and thence, the outer coil is allowed to contract to form an interference fit with the inner coil. The cable may be incorporated as part of various medical systems e.g., implantable pumps or other rotatable medical apparatuses. The cable is bendable about the tight radii, has a high torque transfer, a small outer diameter, and a hollow lumen through which fluid, wires or medial devices may pass.

2 Claims, 31 Drawing Sheets

U.S. PATENT DOCUMENTS

| | | |
|---|---|---|
| 4,545,390 | 10/1985 | Leary . |
| 4,625,712 | 12/1986 | Wampler . |
| 4,632,110 | 12/1986 | Sanagi . |
| 4,646,736 | 3/1987 | Auth . |
| 4,664,112 | 5/1987 | Kensey et al. . |
| 4,676,249 | 6/1987 | Arenas et al. . |
| 4,719,924 | 1/1988 | Crittenden et al. . |
| 4,721,116 | 1/1988 | Schintgen et al. . |
| 4,798,598 * | 1/1989 | Bonello et al. ................... 604/280 |
| 4,906,241 * | 3/1990 | Noddin et al. ................... 606/194 |
| 4,951,677 * | 8/1990 | Crowley et al. ................ 128/662.06 |
| 5,306,252 * | 4/1994 | Yutori et al. ................... 604/164 |
| 5,947,940 * | 9/1999 | Beisel ................... 604/282 |
| 5,951,539 * | 9/1999 | Nita et al. ................... 604/526 |

* cited by examiner

HOLLOW LUMEN CABLE APPARATUS

This application is a divisional application of application Ser. No. 07/959,551 filed Oct. 13, 1992, now U.S. Pat. No. 5,678,296, which is a division of application Ser. No. 07/384,393 filed Jul. 24, 1989, now U.S. Pat. No. 5,154,705, which is a continuation-in-part of application Ser. No. 07/102,878 filed Sep. 30, 1987, abandoned.

BACKGROUND OF THE INVENTION

A cable usable for incorporation in medical apparatus.

It is old to provide a cable by winding one or more strands of wire about a linear central wire in contact with the wire throughout at least a major part of the axial length of the central wire. However with such prior art cables the useful life is shortened due to fracturing of the central wire, particularly when being or relatively tight radii and still satisfactorily transfer torque from one end to the other with high resolution, in part due to the solid core wire taking a set. Additionally it is hard to clean out all of the foreign material entrapped during the manufacture of the solid lumen helical cables.

Oldbergh U.S. Pat. No. 3,267,697 discloses a universal join for automobiles that includes a plurality of multifilar spring units in telescoped relationship. The inside diameter of the intermediate spring unit is slightly less than the outside diameter of the inner spring unit. During assembly the inner unit is preloaded to cause radial contraction and after being inserted into the intermediate unit, is allowed to expand. The radial intermediate coil is wound in the opposite direction from that of the winding of the inner and outer coils. Ruegg Re. U.S. Pat. No. 25,543 and Hotchkiss U.S. Pat. No. 1,228,439 each disclose a flexible coupling member and a flexible shaft respectively which each includes an intermediate coil wound in a direction opposite that of the radially inner and outer coils. Sperling U.S. Pat. No. 1,279,773 also discloses a flexible shaft having oppositely wound coils.

Lerwick U.S. Pat. No. 3,811,446 discloses endarterectomy apparatus that includes an electric motor 11 which drives a pair of springs that in turn drive the input shaft of a converter. The inner coil is multifilar and is enclosed by an outer helical spring. Wampler U.S. Pat. No. 4,625,712 discloses an intravascular blood pump drivenly connected by a flexible shaft to a support unit that is located outside of the human body.

Kline et al U.S. Pat. No. 3,749,036 discloses a guide wire having an outer spring coil that extends between the proximal and distal tips, and in two embodiments an inner coil only in the distal end portion of the outer coil and in two embodiments a wire core extends between the tips.

Each of Takahashi U.S. Pat. No. 4,178,810 and Sanagi U.S. Pat. No. 4,632,110 discloses a coil spring having forceps mounted on one end thereof and a manipulating handle mounted on the other end. Auth U.S. Pat. No. 4,646,736 discloses transluminal thrombectomy apparatus having a shaft comprised of a 3 mil gold wire helically wound about a 4 mil stainless steel arbor for rotating a tip and being driven by a prime mover. Mac Lean U.S. Pat. No. 2,955,592 discloses a medical instrument having a sheath that includes an outer coil and an inner coil. Willson discloses a vascular tissue removing device that includes a single layer multistrand closely spaced helically wound coil of wire (U.S. Pat. No. 3,749,085).

Kensey et al U.S. Pat. No. 4,664,112 discloses a catheter bendable about a radius of curvature, e.g. 3", and having a working head rotated at a high speed by a drive assembly. In one embodiment the drive assembly includes two interlaced helical wires having their distal ends joined to a cutting tip. The two wires are wound about a guide wire to rotate about a guide wire, are of outside diameters of 0.01", and are loosely wound.

Kline U.S. Pat. No. 3,757,768 discloses a spring guide catheter wherein a plastic tube is heat shrunk over a coil spring while O'Neil U.S. Pat. No. 4,145,247 discloses a pacer lead wherein a coil conductor is enclosed in an insulating layer.

Each of Samson et al U.S. Pat. No. 4,538,622 and Leary U.S. Pat. No. 4,545,390 discloses a PCTA guide wire that includes a main wire having a proximal cylindrical portion, a tapered intermediate portion and a cylindrical distal end portion of a smaller diameter than the proximal cylindrical portion and a helically wound coil having a proximal portion joined to the tapered portion, and a distal tip joined to one or both of the main wire distal end and the coil. In Samson the coil includes two coil portions of different materials.

U.S. Pat. No. 4,516,972 to Samson discloses a guiding catheter that includes an inner liner, a first plurality of ribbons helically wound on the inner liner, a second plurality of ribbons helically wound in the opposite direction on the first ribbons and an outer plastic jacket. The helices of the ribbons are different pitches in different regions along the length of the inner member.

One of the problems encountered in the prior art is the lack of a very small diameter, highly flexible cable that has a relatively long life even when bent about relatively small radii for forming a part of medical apparatus, for example rotating or otherwise moving all or part of a medical device or medical subassembly and is medically clean. In order to overcome problems such as the above as well as others this invention has been made.

SUMMARY OF THE INVENTION

Hollow lumen cables that are usable for driving medical devices, or mounting medical devices that include a multifilar inner coil that in a non-assembled relaxed condition is of a given outer coil diameter that is larger than that of the outer coil inner diameter wherein in an assembled condition the inner and outer coils are oppositely wound with the outer coil inner peripheral surface being in an interference fit relationship with the outer peripheral surface of the inner coil. The cable may be used for forming a drive connection between a powered prime mover and a pump mountable in a human body, or driving an atraumatic tip or have a manually manipulated handle mounted on one axial end and, for example a forceps mounted on the opposite end, or form a part of a guide wire. Advantageously the outer coil may be of an outer coil diameter of about 1/16" or less. The cable also may be used in forming a catheter.

One of the objects of the invention is to provide a new and novel hollow lumen cable for use in the medical field. In furtherance of the above object it is another object of this invention to provide a new and novel method of making such a cable. Another object of this invention is to provide a new and novel cable usable in the medical field that is of a relatively small outer diameter, and can form a drive connection that is rotatable at relatively high speeds with high torque resolution even when bent about relatively tight radii of curvature including through a circle and is medically clean. Still another object of this invention is to provide new and novel guide wire means that incorporates the cable of this invention.

A different object of this invention is to provide a new and novel catheter that has very good torque transmitting characteristics. An additional object of this invention is to provide a new and novel guide wire having a main wire and a spring coil, and the method of making such a guide wire.

For purposes of this application a "hollow lumen cable" relates to a cable wherein none of the strands of helically wound wires are wound around and in contact with a linear central wire (mandrel). Further for the purposes of this application "press fit" refers to the relationship between a coil and a guide wire main wire wherein the coil in its relaxed condition has a smaller inner diameter than the outer diameter of at least a major part of the axial length of the portion of the main wire that is thereafter extended into the coil, and the coil is partially unwound to have an inner diameter that is larger than the outer diameter of the main wire that is to be extended into the coil, the force retaining the coil in its partially unwound condition is released to allow the coil to resiliently return toward its fully relaxed condition to form a clamping fit with the radially adjacent part of the main wire that is to be engaged thereby which is of a large diameter than the inner diameter of the coil prior to the partial unwinding of the coil.

In the event that a coil spring is formed by winding a coil wire around an axial cylinder portion of a guide wire main wire, upon the release of the winding force the wound coil expands, even if tightly wound around the main wire. Accordingly when turning the main wire, whipping of the distal end takes place, provided the main wire is not of an undesireable degree of stiffness, or a relatively large diameter. Such whipping takes place even if the proximal end and at least part of the distal end portion of the coil is brazed, soldered or similarly fixedly secured to the main wire. Even if the coil were brazed to the main wire before releasing the unwinding pressure the coil would be in intimate fitting relationship to the cylindrical portion of the main wire that the coil was in abutting relationship with and as a result there would be an undesirable amount of stress in the coil. Additionally such whipping occurs if the coil is formed to have an inner diameter only slightly larger than the maximum diameter of the cylinder portion of a guide wire main wire that is to be extended into the coil, and after the formation of the coil and sliding the main wire to extend into the coil, the coil proximal end and distal end portions are brazed or similarly fixedly secured to the main wire. The term "press fit" as used in this application does not include the methods referred to in this paragraph.

BRIEF DESCRIPTION OF THE INVENTION

Figure 29:
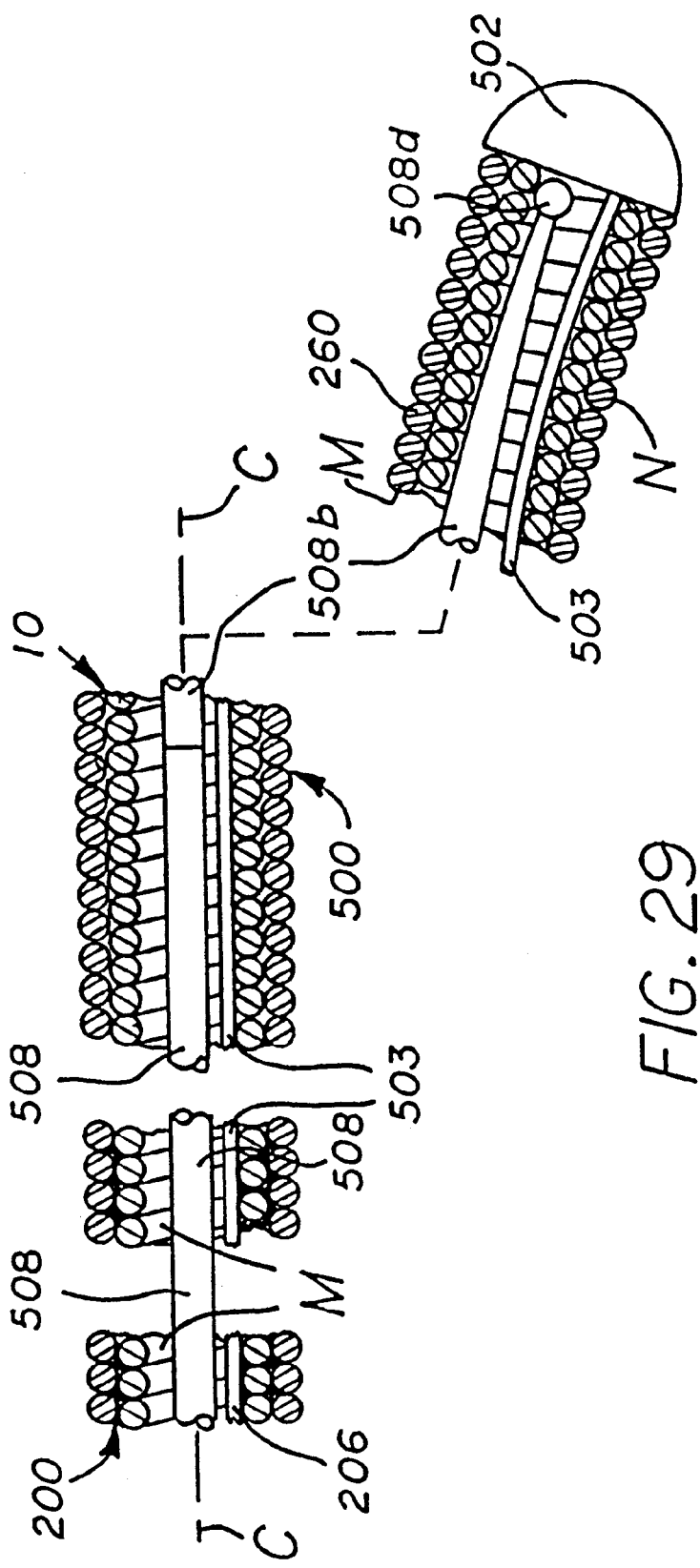
Figure 30:
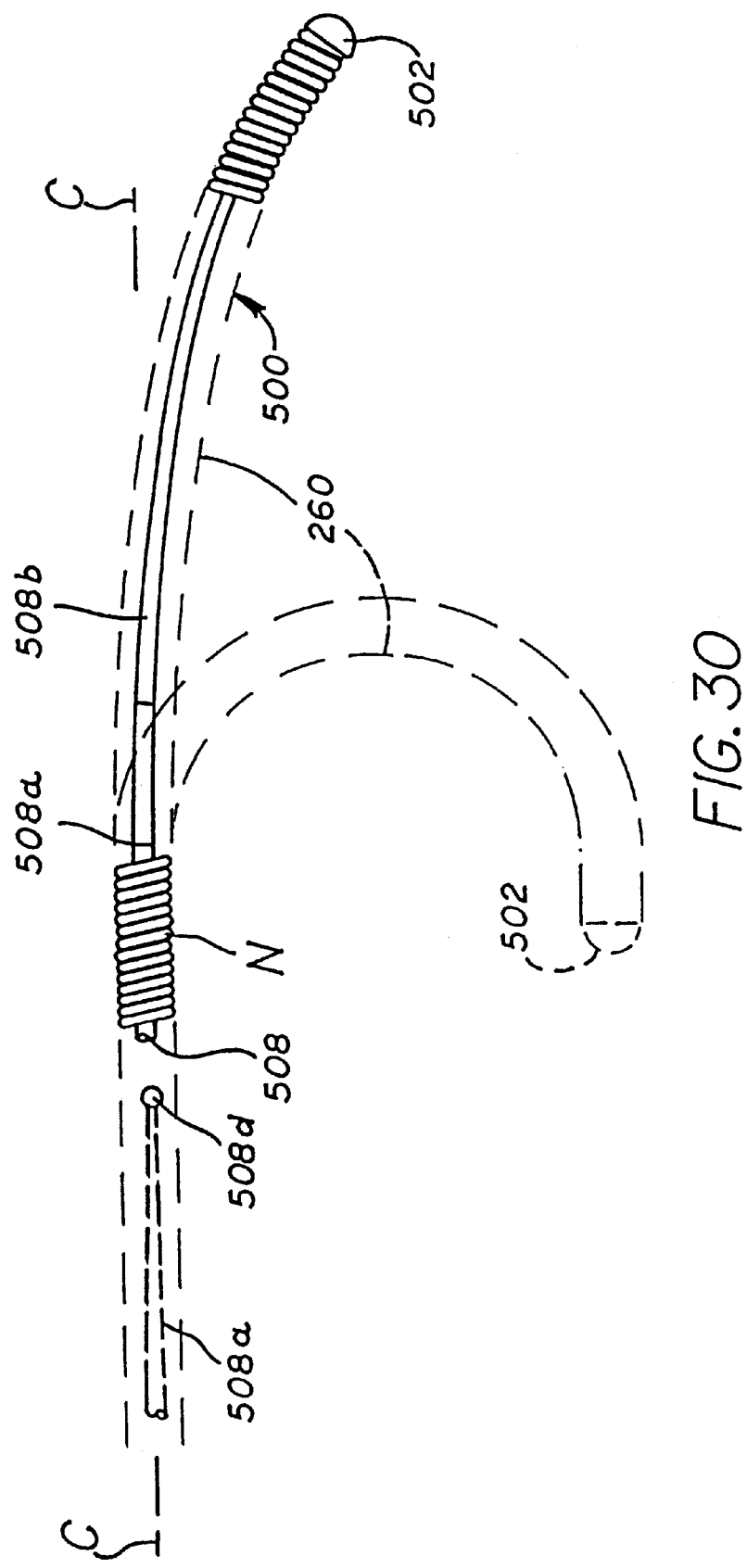

FIG. 29 is a fragmentary showing of the twelfth embodiment of the guide wire of this invention that is the same as the sixth embodiment other than for the distal end portion of the core wire and the resulting curvature of the guide wire with the core wire in its extended position; only the proximal and distal parts of the cable assembly and radially adjacent parts of the core wire being shown; and FIG. 30 is a fragmentary view of the distal end portion of the guide wire of FIG. 29 that shows the core wire in its extended position in solid lines together with the resulting curvature of the distal end portion of the cable assembly; and the core wire in its retracted position in dotted lines together with the distal end portion of the cable assembly in its datum J-shaped configuration; the axial length of the distal end portions relative to their diameters being exaggerated.

Figure 31:
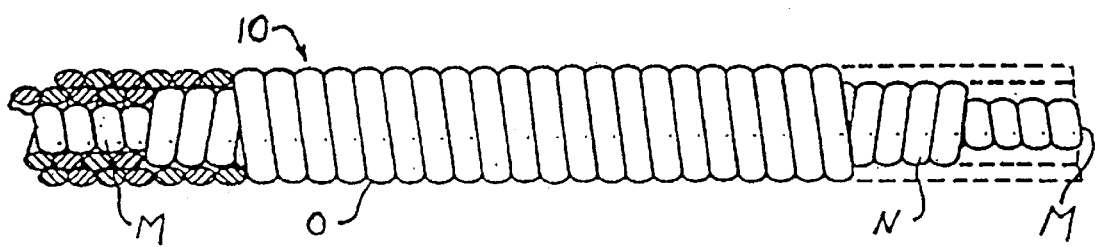

FIG. 31 shows in partial section a 3 coil embodiment of the present invention.

Figure 1:
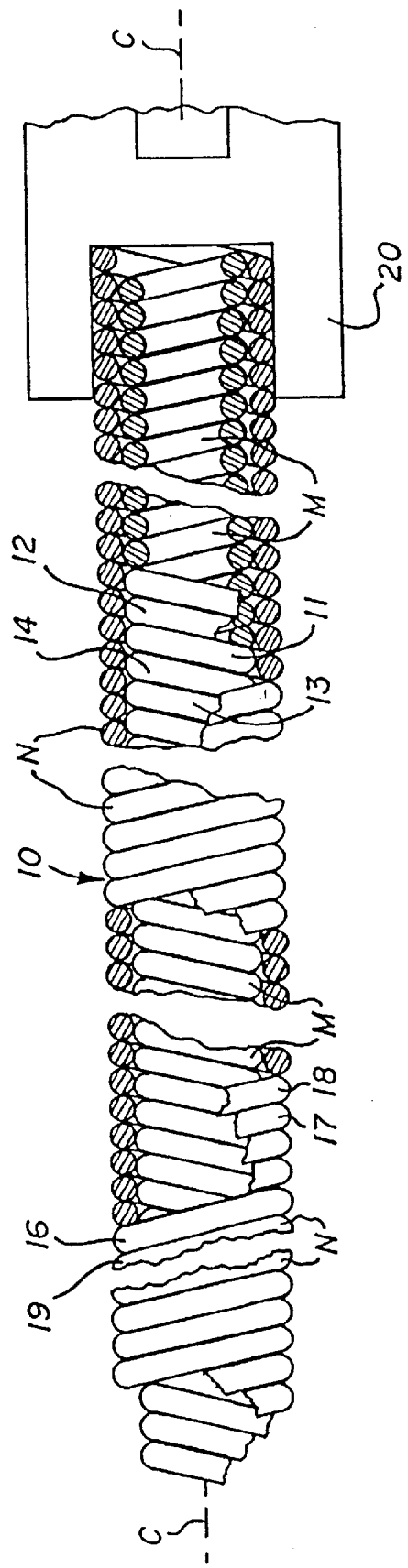
FIG. 1 is in part a side view, in part a cross sectional view through the outer and inner coils and in part a cross sectional view through the outer coil and a side view of the inner coil of the cable of this invention and a cross sectional view through a part of a connector or coupling, a number of axial intermediate parts being broken away.
Figure 2:
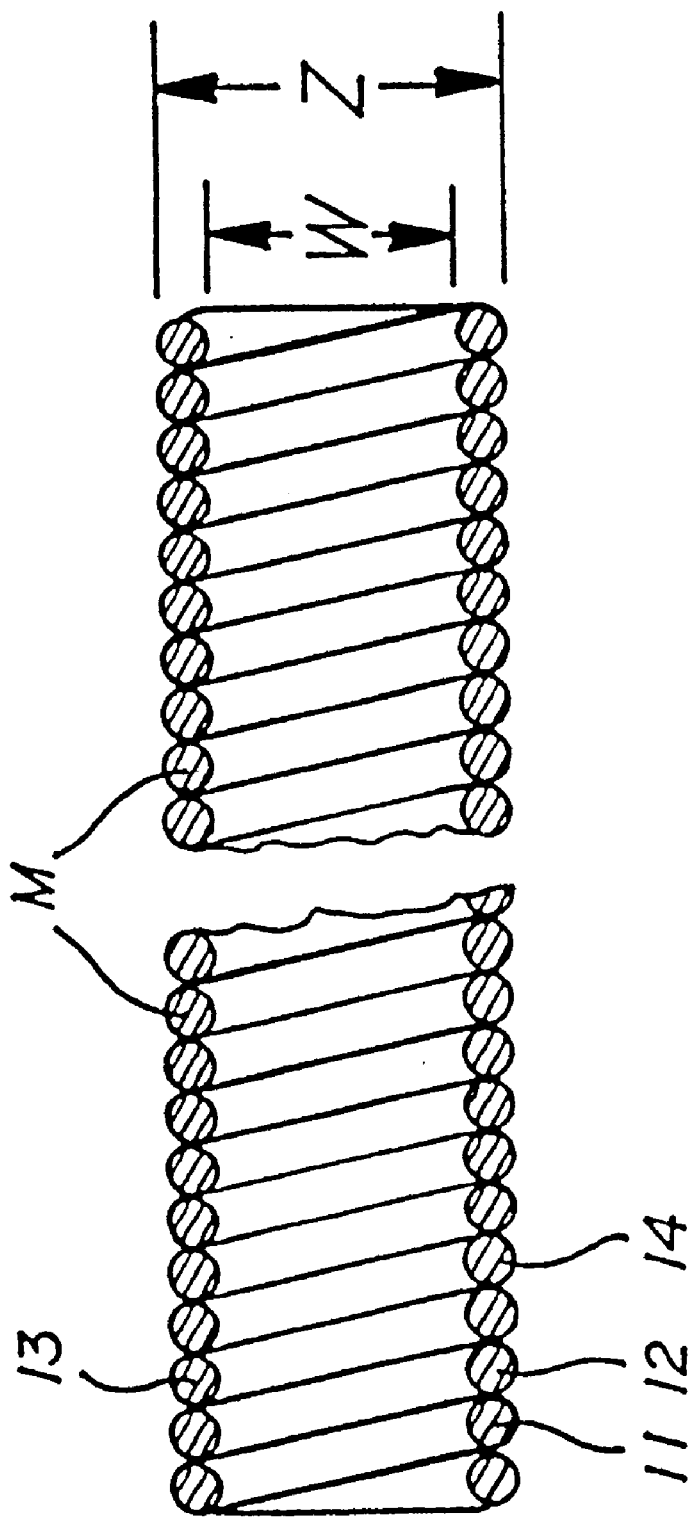
FIGS. 2 and 3 are fragmentary cross sectional views of the inner coil and outer coil respectively in their relaxed non-assembled conditions.
Figure 3:
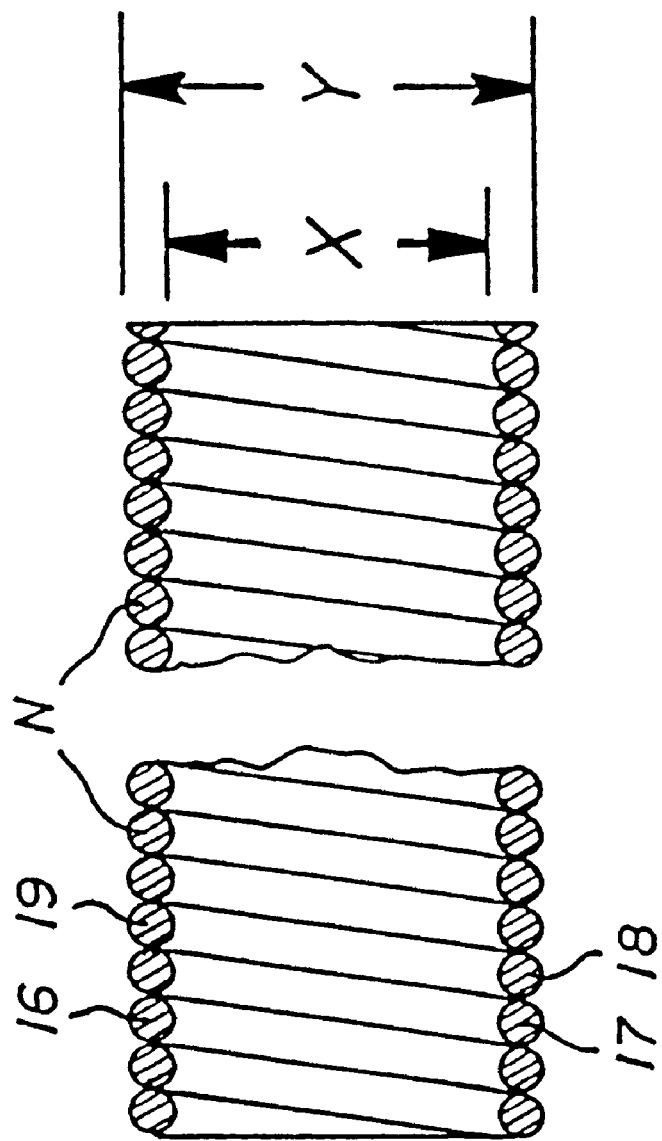

Referring to FIGS. 1–3, the hollow cable of this invention, generally designated 10, includes an inner coil M made up of a single layer of multifilar helically wound coil of wires, preferably four wires 11, 12, 13 and 14 that has each convolution (helice) of one wire in contact with the adjacent convolution of two other wires. The inner coil is wound to in a relaxed non-assembled condition have a coil inner peripheral diameter W and a coil outer peripheral diameter Z. The cable 10 also includes an outer coil N made up of a single layer of multifilar helically wound coil of wire, preferably four wires 16, 17, 18, 19 that are wound in the opposite direction from the winding of the inner coil, and likewise has adjacent wire convolutions in contact with one another. The outer coil is wound to in a relaxed non-assembled condition have a coil inner peripheral diameter X and a coil outer peripheral diameter Y. For example the inner coil outer peripheral diameter in a non-assembled condition may be about 0.002" greater than the outer coil inner peripheral diameter in a non-assembled condition.

For medical uses, prior to winding each of the coils, each strand of wire is cleaned to remove any foreign material on the wire strands and then the desired number of cleaned strands are simultaneously wound to form the respective coil. After the inner and outer coils have been formed, each of the inner and outer coils are cleaned to remove any foreign material on the coils. Subsequent to cleaning the coils, the coils are assembled as set forth below and then the assembled cable is cleaned. Further if after forming the cable, a coupling, medical device or other structure is joined to the cable, the cable with other structure joined thereto is cleaned. Each of the cleaning steps are carried out such that strands of wire, coils and cable are medically or surgically clean.

In order to assemble the cable, the outer coil is partially unwound by applying an unwinding force to increase the coil inner peripheral diameter. Then the inner coil is inserted into the partially unwound outer coil and thence the unwinding force that was applied to the outer coil is released. The axial central part of the outer coil starts to shrink first to form an interference fit with the inner coil and continues to shrink its outer coil diameter toward the outer coil opposite ends whereby there is obtained an interference fit throughout the entire axial length of the cable. All of the helices of each of the coils in the assembled condition of the coils are of substantially the same inner and outer diameters throughout the axial lengths of the coils while the inner and outer coils are of substantially the same axial lengths. That is the helices of each coil are of substantially the same radial spacing from the respective coil central axis C—C.

Forming the cable in the manner set forth herein, it is not necessary to solder or otherwise join the ends of the strands of wire of each coil at either axial end, or the coils to one another to maintain the cable in an assembled condition (no unwinding of the strands). Rather the cable may be shipped for later incorporation with other components or for use. Even if the cable is cut into, for example two axial half sections, the strands at either end of the half sections will not unwind. This is in contrast to prior art solid wire helically wound cables wherein the wire is in tension in abutting relationship to the central core wire and not welded or soldered at various axial positions to the central core wire, or in hollow lumen cables where there is no interference fit between radially adjacent coils throughout their axial lengths. Depending upon the use to be made of the cable of this invention, the distal ends of the strands of wire of the inner coil and the outer coil may be suitably joined to one another by, for example brazing, soldering to round off sharp ends, or to a suitable coupling member 20 such as shown in FIG. 1, or to a member for connecting the distal end to other structure. Likewise the proximal ends of the strands of wire of the coils may be joined. The coupling 20 that is shown in FIG. 1 is particularly suitable for forming a keyed connection to a shaft that is to be driven or provide a driving force. Due to the interference fit of the inner and outer coils throughout their axial lengths there is substantially a 1 to 1 transmittal of torque from one end of the cable to the other regardless of the direction of rotation of the cable.

If one were to exert a winding force to the inner coil to reduce its outer coil diameter or leave the inner coil on a mandrel in a non-relaxed condition, then insert the reduced diameter or non-relaxed inner coil into the outer coil, and thence release the winding force that was applied to reduce the inner coil outer diameter or allow the inner coil to expand on the mandrel, the inner coil expands its outer diameter from its axially opposite ends toward the center. However due to the axially opposite ends expanding first, the axially opposite ends form an interference fit with the outer coil and as a result the inner coil stops expanding before the inner coil axially intermediate portion has fully expanded. During use of the thus formed cable the inner coil gradually turns relative to the outer coil and strands of the inner coil become misaligned with reference to the outer coil. This results in the cable failing in a substantially shorter period of time when the cable is made such as described in the preceeding two paragraphs.

Figure 4:
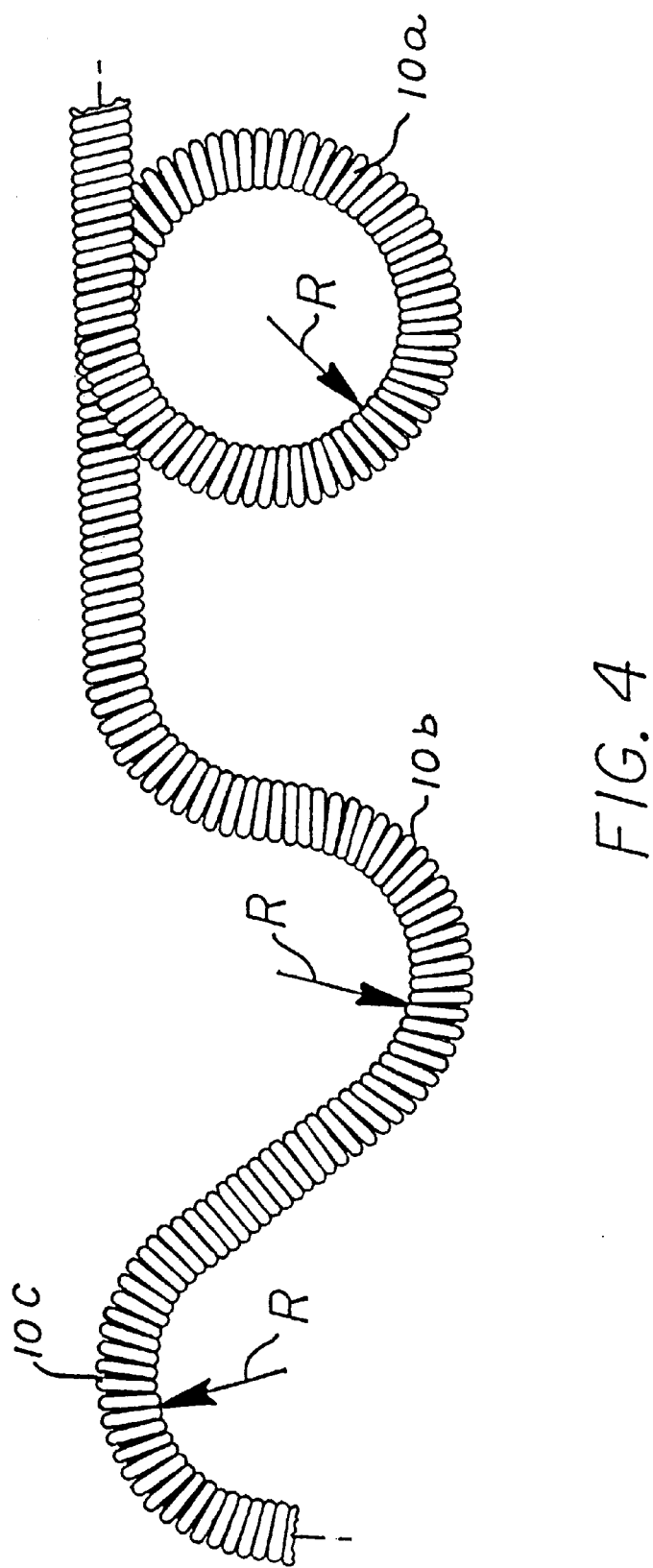
FIG. 4 is a side view of a part of an axial length of the cable of this invention for purposes of indicating the flexibility of this invention.

By assembling through partially unwinding the outer coil and allowing it to contract after the inner coil has been inserted, the cable 10 may be made of an outer diameter of about 1/16" or less and bent through, for example a circular configuration portion 10a of a radius of curvature R of, for example about 1" or/and "S" curved portions 10b, 10c radii of curvature such as indicated (see FIG. 4). Such a cable may be, for example 5 to 15 ft. long and have one end coupled to a motor and an opposite end coupled to a pump to be rotated at, for example 20,000 rpm and the part of the the cable forming the circular portion being spaced from the coil parts completing the circular configuration by less than the cable outer diameter. That is the cable may be extended through a very tortious path when being used without taking any significant set such as occurs with solid lumen cables. The cable may be passed through tortious bends such as found in cardiac and vascular systems and rotated at relatively high speeds if located within a catheter.

The cable 10 may be incorporated in medical apparatus 8 to form a drive connection from a prime mover (motor) 30 having a drive shaft 31 to, for example a heart pump 32 that has a drive shaft 33 or another type of medical device, for example a cylindrical atraumatic tip such as disclosed in U.S. Pat. No. 4,646,736 to Auth. If the cable is to be used to form a drive connection, a suitable connector (coupling) 35 is soldered or otherwise fixed to the distal ends of strands of the coils and is adapted to be removably connected to the motor shaft while a suitable connector (coupling) 36 is similarly fixed to the proximal ends of strands of wire of the cable coils. The couplings are keyed or otherwise attached to the shafts 31, 33. The pump and motor may be of the type disclosed in and used in the manner disclosed in U.S. Pat. No. 4,624,712 to Wampler and thus it is believed there is no need to further disclose the operation of medical apparatus P.

Figure 5:
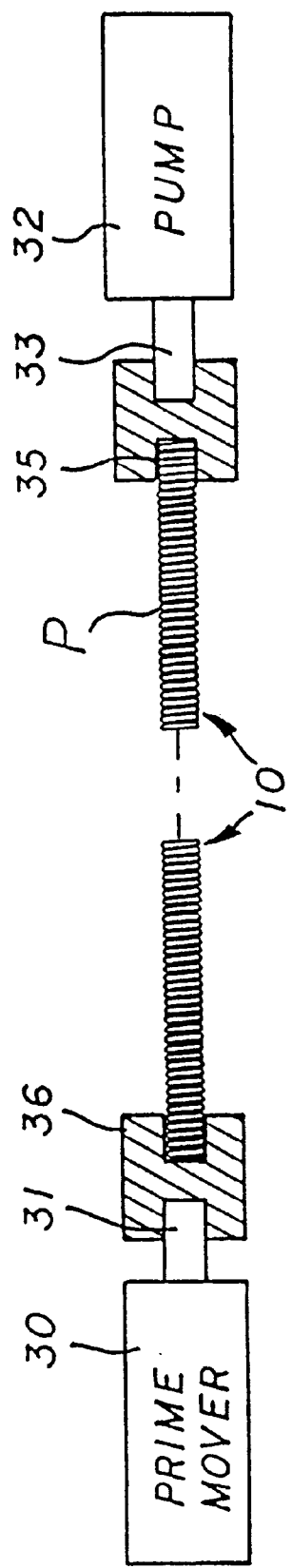
FIG. 5 is a side view of power driven medical apparatus that includes a prime mover, heart pump and the cable of this invention.

In place of members 32, 33, 35 as previously described, the cable 10 may be extended into a catheter tube (not shown) to drive a working head or cutter member (not shown) mounted by the catheter tube distal end portion for high speed rotation such as disclosed with reference to FIG. 5 of Kensey U.S. Pat. No. 4,664,112. That is the cable 10 may be driven by motor 30 and advantageously used in place of the two helically wound, interlaced wires to drive the working head of Kensey, with a guide wire extended into the lumen of cable 10 or without a guide wire extended into the lumen.

Figure 6:
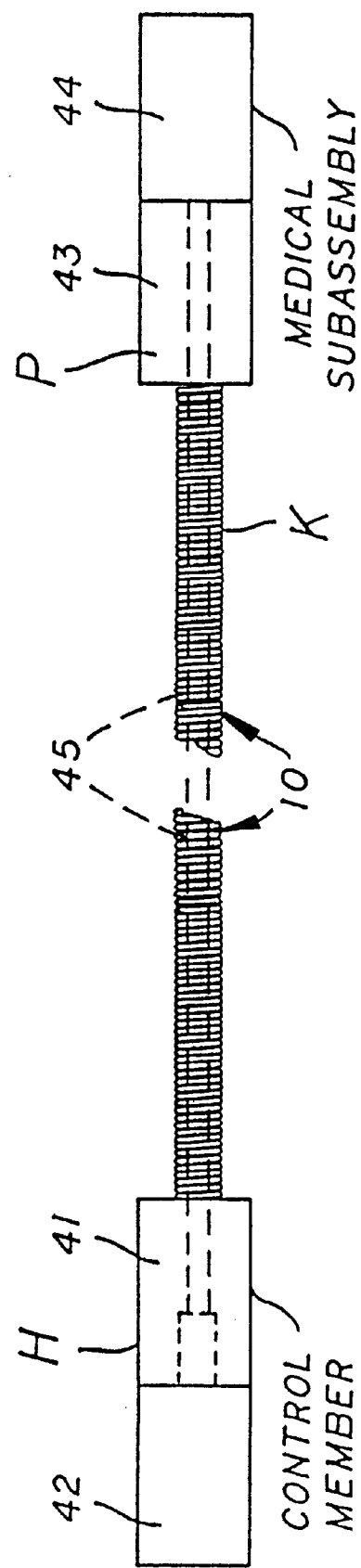
FIG. 6 is a side view of manually operated medical apparatus that includes a control member, a medical subassembly, for example a cutter or forceps and the cable of this invention mounting the control member and medical subassembly, the control member and medical subassembly being diagrammatically illustrated.

Referring to FIG. 6, the medical apparatus K includes a cable 10 that has its proximal end portion fixedly attached to the manually operated control member H while the distal end portion mounts a medical subassembly D, the control member and medical subassembly being diagrammatically illustrated. The device D may be of a type that only moves when the cable moves and does not have one operative part movable relative to another part. That is the device may be a tissue scraping tool such as shown in FIG. 1 of U.S. Pat. No. 3,749,085 to Willson et al and welded or attached by a suitable connector 43 to the distal end portions of the strands of the cable coils while the control member may be a single part member for rotating and/or pushing the cable through a catheter. The control member H may include a manipulator portion 42 that corresponds to element 29 of Willson, a finger grip portion 41 corresponding to portion 30 of Willson and a cutter device D that corresponds to the scraper mechanism shown in FIG. 1 of Willson and mounted on the distal ends of the strands of wire of the cable by the scraper mechanism being soldered or brazed to a connector (not shown) which in turn is suitably fixed to the distal end of the cable 10. By using the cable 10 there is no need to provide a core wire such as provided in Willson.

As another alternative the medical instrument K may be of a type that the subassembly D may be a forceps or cutter having one or more parts 44 movable relative to another part 43 which is fixedly attached to the cable wire distal ends. The movable part (parts) 44 may be moved relative to part 43 by a core member 45 which extends through the cable hollow lumen and is of a substantially smaller diameter than the inner diameter of the inner coil M. The proximal ends of the cable coils are mounted to the hand grip portion 41 of the control member H while the proximal end of the core member is mounted to the manipulator portion 42 of the control member H. The manipulator portion is manually movable relative to the hand grip portion for moving the core member and thereby the medical device part 44 relative to part 43. The apparatus K may be of the general nature disclosed in U.S. Pat. Nos. 4,178,810 or 4,632,110 wherein the part 44 is forcep cups, part 43 a tip mounting the cups and being mounted on the distal end portion of the cable 10, the cable taking the piece of the coil sheath of these patents, and the core member 45 being connected to the plunger 42 for operating the forcep cups 44. That is the cable 10 may be used in place of the coil sheath of U.S. Pat. No. 4,632,110 and have the distal ends of its strands attached to the tip which mounts the forceps cups. It is believed in view of the above description and if necessary a reference to either of U.S. Pat. Nos. 4,178,810 or 4,632,110 it is not necessary to further describe the operation of this alternative form of apparatus K.

Figure 7:
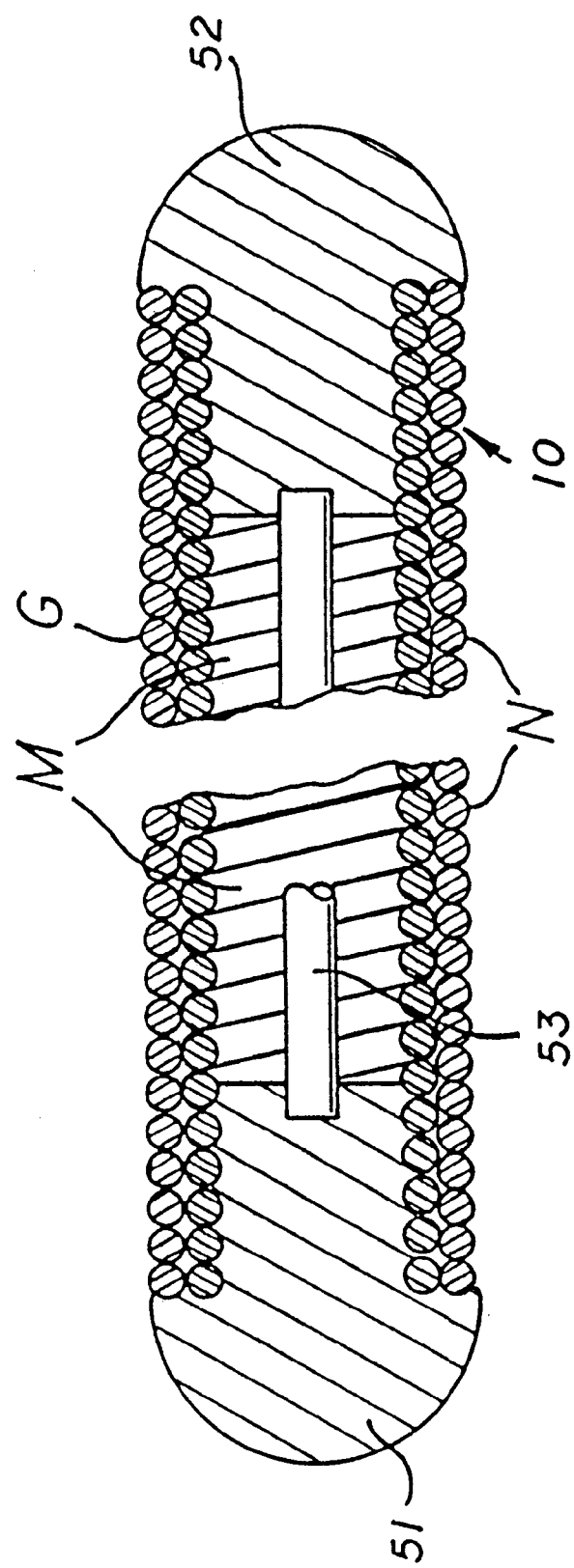
FIGS. 7–11 are cross sectional views of five embodiments of guide wires incorporating the cable of this invention with the axial intermediate portions being broken away.

Referring to FIG. 7, the medical apparatus G comprises a guide wire that comprises a cable 10 having a proximal guide wire tip 51 attached to proximal ends of the cable wires, for example by welding or soldering, while a distal guide wire tip 52 is similarly fixedly attached to the distal ends of the cable wires. A core wire (main wire) 53 is optionally extended through the cable to have its opposite ends joined to the adjacent tip 51 and 52, the diameter of the core wire being significantly smaller than the inner diameter of the inner coil M. Because of the torque transmission capabilities of the cable of this invention, there is need to solder various axial intermediate parts of a core wire (if provided) in order to properly transfer torque from the guide wire proximal tip to the distal tip if such tips are provided at axially opposite ends of the guide wire as shown in FIG. 7. The guide wire G may be used in a conventional manner, for example see U.S. Pat. No. 3,749,086.

Figure 8:
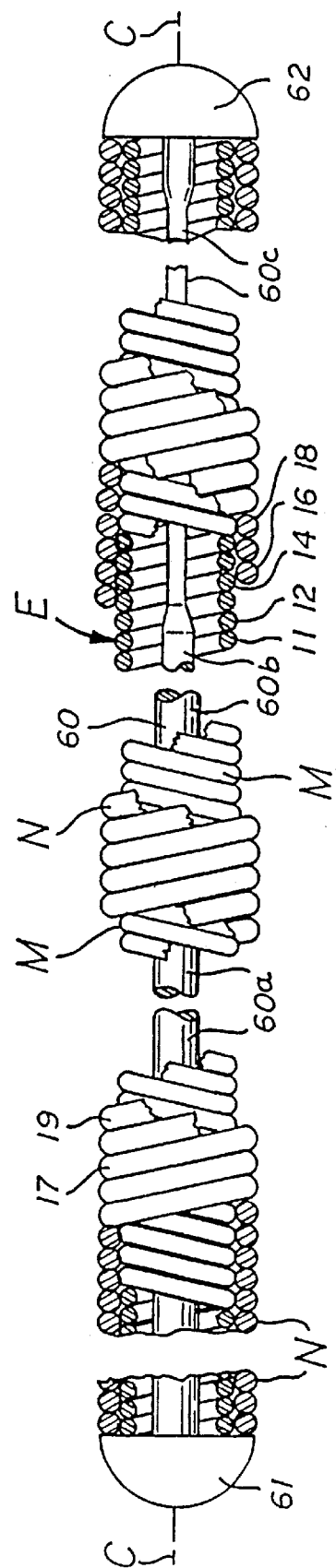

Referring to FIG. 8, a second embodiment of the guide wire of this invention, generally designated E, is similar to that disclosed with reference to FIG. 7, other than for the main wire core wire or member 60 and embodiment E is a high strength guide wire. The main wire 60 has a proximal cylindrical portion 60a having its proximal end joined to the proximal tip 61 which in turn is joined to the cable proximal end portion. The distal end of the main wire is integrally joined to the major base end of the frustoconical axial intermediate (tapered) portion 60b of the main wire while the distal end of the intermediate portion is integrally joined to the distal cylindrical portion 60c of the main wire, portion 60c in turn being joined through a main wire distal terminal end portion 60d. Portion 60d may be flattened, and is joined to the cable distal end by the distal tip (bead) 62.

Figure 9:
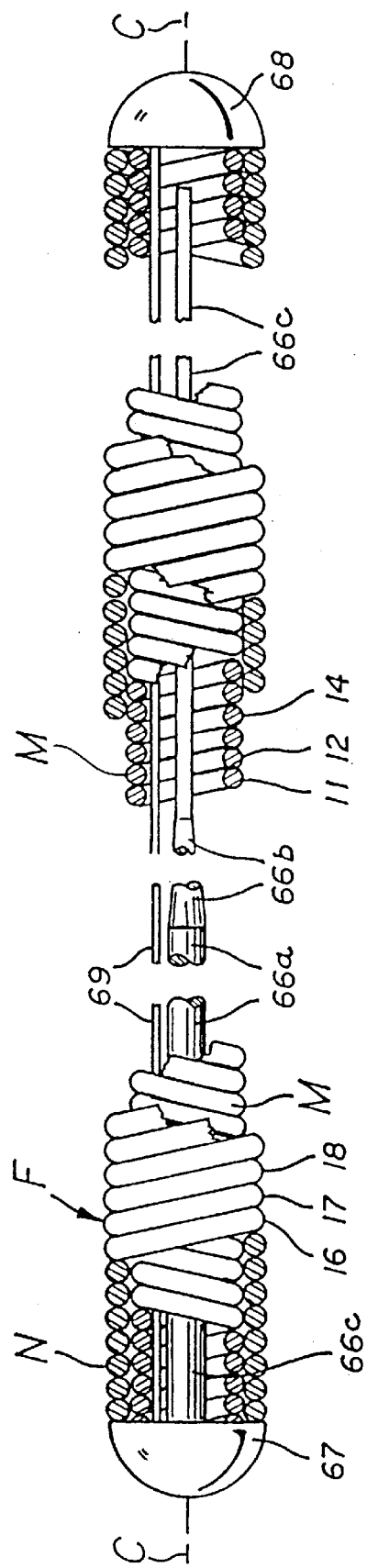

Referring to FIG. 9, the third embodiment of the guide wire of the invention, generally designated F, is similar to that disclosed with reference to FIG. 8. That is, the main wire 66 of embodiment F has a cylindrical portion 66a, an axially intermediate (tapered) portion 66b and cylindrical portion 66c that correspond to portions 60a, 60b respectively. The main wire proximal end is joined to the proximal ends of cable 10 (coils M,N) by a proximal tip 67 while a distal tip 68 is joined to the distal ends of the coils with the main wire extending through the hollow lumen of the cable. However the distal terminal end of distal portion 66c terminates short of the distal tip. A safety wire 69 is provided within the hollow lumen of the cable and has its proximal and distal ends joined to the proximal and distal tips respectively.

Figure 10:
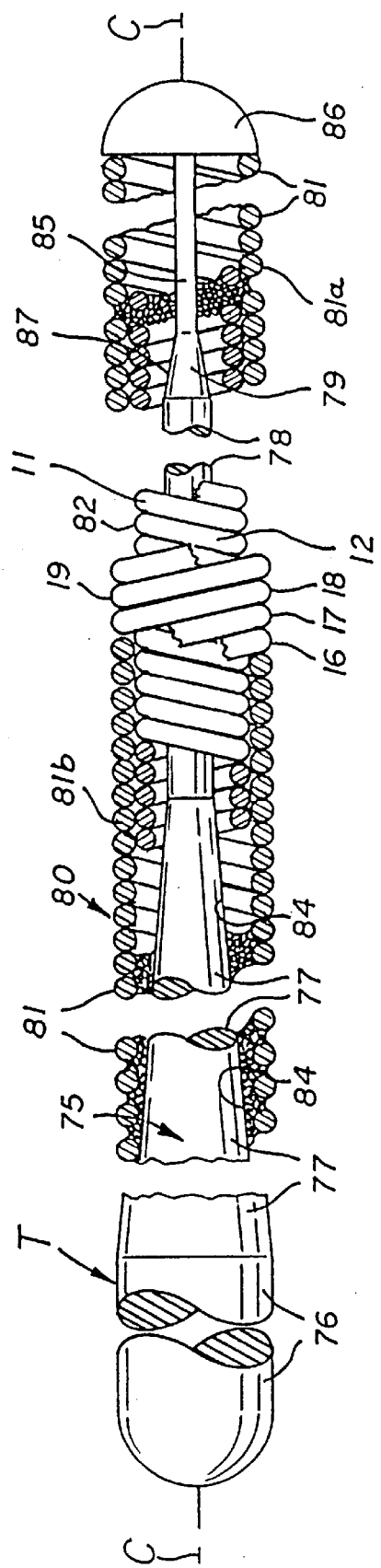

Referring to FIG. 10 there is shown a PTCA guide wire of this invention, generally designated T, that includes a main wire, generally designated 75 which has a proximal cylindrical portion 76 that at its distal end is integrally joined to the major base of the first frustoconical tapered (axially intermediate) portion 77 while the minor base of portion 77 is integrally joined to the second cylindrical portion 78. The cylindrical portion 78 is of a substantially smaller diameter than that of portion 76.

As shown in FIG. 10, a cable, generally designated 80, is a modified form of cable 10 which is formed in the same manner as cable 10 except the outer coil 81 is of a longer axial length than the inner coil 82. The proximal end portion of the inner coil and the radially adjacent part of the outer coil are brazed or otherwise suitably joined to the tapered portion 77 at 83 while the proximal end portion of the outer coil likewise is suitably joined at 84 to the tapered portion. The taper of the tapered portion, the axial distance the outer coil extends more closely adjacent to the proximal terminal end of the main wire than the inner coil, and the axial spacing of the terminal ends of the coils is such that the outer diameter of the outer coil is substantially the same as that of the proximal cylindrical portion and is substantially of the same outer diameter throughout its axial length. The inner diameter of the inner coil is sufficiently great that there is an annular space between the inner coil and the cylindrical portion. Further the inner coil throughout its axial length is in interference fitting relationship with the outer coil.

The second cylindrical portion is integrally joined to the major base of the second frusto-conical portion 79 which in turn has a minor base integrally joined to the proximal end of the distal end portion 83. The distal end of portion 85 is joined to the guide wire distal tip. Portion 85 may be circular cylindrical or rectangular in transverse cross section. Portion 85 is of a substantially smaller transverse cross sectional area than that of the second cylindrical portion which in turn is of a substantially smaller diameter than that of portion 76. The distal end of the inner coil and the radially adjacent part of the outer coil is brazed or otherwise suitably joined at 87 to either one or both of portions 79, 85, advantageously adjacent to the juncture of portions 79, 85. The axial length of the outer coil in a distal (forward) direction may be sufficiently greater than that of the inner coil to extend from the brazing 87 to the distal tip 86 to be joined thereto. That is the outer coil may have a first coil portion (third coil) 81a joined to and extended from brazing 87 to the distal tip 86 and integrally joined with the second coil portion 81b as one unitary coil. However, advantageously the distal terminal ends of the inner and outer coils of cable 80 are of substantially the same axial spacing from the distal tip and a third coil 81c (fifth embodiment—FIG. 11); which may or may not be of the same material as coil portion 81b and may or may not be multifilar; has its distal end joined to the distal tip 86 and its proximal end joined to brazing 87. In such an event coil portion 81b would be in interference fitting relationship with the radially adjacent parts of coil 82.

In place of wire 75 having an intermediate portion 77–79 described above, portion 77–79 may be modified such that the portion 77–79 may be of the same diameter throughout its axial length as portion 78 and integrally joined to portion 76 to form an annular radial shoulder with both the inner and outer coils extending in a rearward direction to have their proximal ends abut against or be closely adjacent to such a shoulder and be brazed or otherwise suitably joined to one or both the cylinder portion 77 and the modified intermediate portion without the coils otherwise being joined to the main wire, except as brazing 87. The outer diameter of the outer coil with the modified intermediate portion would be substantially the same as that of portion 76.

It is to be noted the outer coil of cable 80 may have its proximal terminal end radially adjacent to the inner coil proximal terminal end and in such an event brazing or other material may be provided on the tapered portion axially between the cylinder portion and the proximal coil terminal ends to avoid an abrupt change of the coil distal terminal ends and the radially adjacent part of the main wire tapered portion.

As an example of the guide wire of this invention, but not otherwise as a limitation thereof, the main wire 66 of the embodiment F of FIG. 9 may be of a length of about 50–400 cm, portion 66b of a length of about 3.5 cm, portion 66c of a length of about 3.5 cm and of a diameter of about 0.004" or 0.005", and portion 66a of a diameter of about 0.010"–0.018". Similarly as an example of the embodiment of FIG. 10, the length of the main wire may be about 180 cm, the proximal cylindrical portion of a diameter of about 0.012"–0.018", tapered portion 77 of a length of about 2 cm, portion 78 of a length of about 28 cm and a diameter of about 0.008", portion 79 of a length of about 2 cm and if circular, a diameter of about 0.003" (advantageously flattened to have a major transverse dimension substantially less than the inner diameter of the inner coil) and coil portion 81a of an axial length of about 2 cm. Thus the axial length of the proximal cylindrical portion 76 is substantially greater than the combined axial length of portions 77–79 and 85. The outer diameter of each of the outer coils of the guide wires of this invention advantageously are less than $\frac{1}{16}$", and whereby the guide wire incorporating the cable of this invention is suitable for use as a vascular guide wire. The diameter and length of the various parts of the guide wire would depend upon the particular use to be made of the guide wire.

Figure 12:
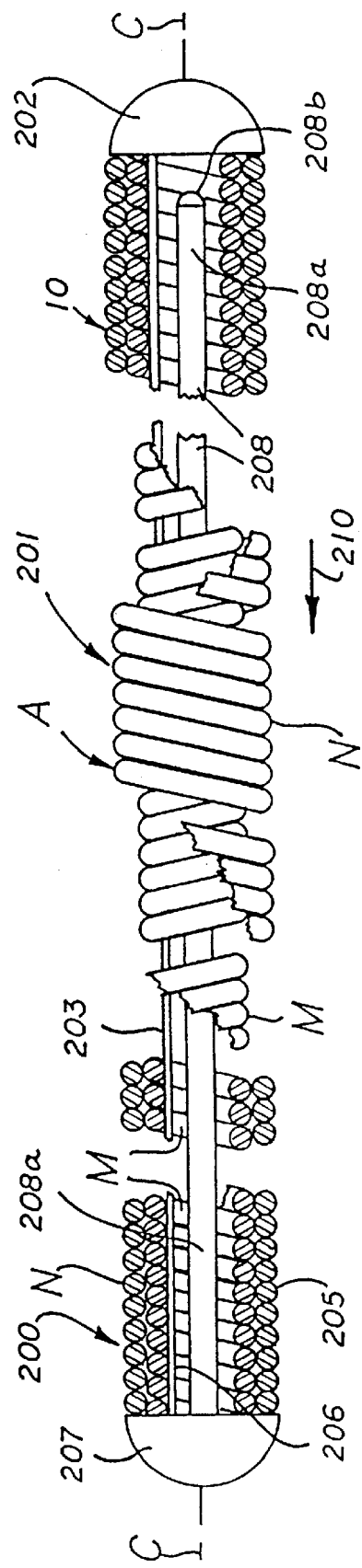
FIG. 12 is a view similar to FIG. 8 other than it is of a sixth embodiment of the guide wire of this invention which is of a J-type with the core wire in a position to straighten the distal J-portion.

Referring to FIG. 12, the sixth embodiment of the guide wire of this invention, designated A, includes a core wire assembly generally designated 200 and a cable assembly, generally designated 201. The cable assembly includes a cable made up of coils M, N having a guide tip (bead) 202 joined to the distal end of the cable wires, for example by soldering and a safety ribbon 203 that extends within the cable inner coil M and radially adjacent to the inner peripheral wall thereof. The safety ribbon has its distal end joined to the bead 202 and its proximal end joined to the proximal end of the inner coil M, and/or the outer coil N, for example by soldering. The ribbon distal end may be joined to the bead 202 by welding at the time the bead is formed. The distal ends of the wires of the cable (coils M, N) may be joined to the bead at the time the bead is formed.

Figure 15:
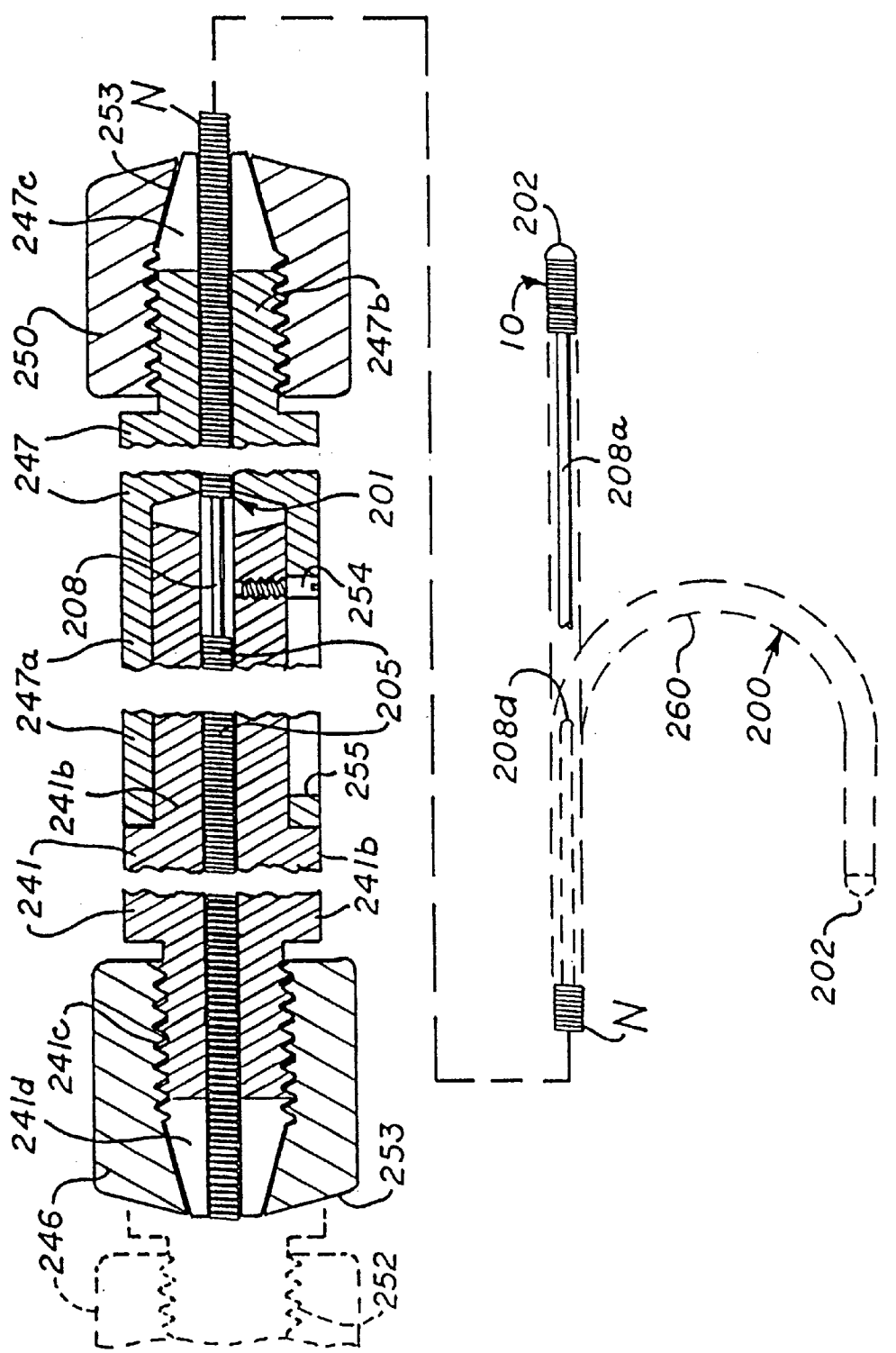
FIG. 15 is an enlarged cross sectional view of FIG. 13 with axial intermediate portions broken away and the distal part of the guide wire of FIG. 12 in its straightened condition in solid lines and in its flexed J-shaped condition in dotted lines.

The cable assembly 201 is formed such that upon sufficiently retracting the core wire assembly the flexible distal end portion 260 will assume the generally J-shaped (datum position) shown in dotted lines in FIG. 15, i.e. resiliently assume such a shape, but if only partially retracted, will be arcuately curved between the two positions shown in FIG. 15. The amount of curvature depends upon the amount of retraction and the construction of the distal portion of the core wire used for forcing the J-portion 260 toward a more nearly linearly extending condition. Even though the entire length of cable M, N of the cable assembly and core wire 208 will flex downwardly axially away from the proximal end when the proximal end is held to extend horizontally, the showing of the two positions of the J-portion in FIG. 15 being relative positions when using a core wire of a constant diameter other than at the distal tip and possibly at the proximal tip. As an example, but not otherwise as a limitation the J-portion 260 from the point where it starts to curve relative to the remainder of the cable assembly to the distal terminal end of the distal tip of the core wire generally is in the range of about 1 to 5 cm. Thus the total length of the cable assembly into which the core wire is extended is several times greater than the length of portion 260 and frequently is well over ten times the length of portion 260.

The core wire assembly 200 includes a cable section 205 formed by coils M, N and is the same as that previously described other than its axial length is several time shorter than that of the cable assembly, a safety wire 206 having its distal end joined to the distal end of the inner coil M, and a proximal bead 207 joined to the proximal ends of the core wire 208, and the proximal ends of the wires of cable section 205. Desirably the core wire is joined to the partial spherical bead 207 radially off center from the central axis c—c of the guide wire.

The core wire 208 of assembly 200 is of an axial length that when extended within the guide wire cable of assembly 201 will have its distal end abut against the bead 202 and the proximal terminal end of the cable assembly axially spaced from the distal terminal end of the cable section 205 while the cable section is fully relaxed and the cable distal J-portion is in its straightened position such as shown in solid lines in FIG. 15. Desirably the core wire has an axially elongated cylindrical portion 208a that is joined to the bead 207 and extends axially therefrom to the distal terminal bead (tip) 208d. The distal tip 208d may be the distal end portion of the core wire that is rounded to be of a generally hemispherical shape or a separated bead joined to the distal end of the core wire and of a radius of curvature that is the same as the radius of curvature as that of portion 208a. Portion 208a is of a constant diameter from bead 207 to tip 208d. Further the core wire is of sufficient rigidity to force the normally J-shape portion to its generally straightened shape of FIG. 15.

The core wire assembly cable section, safety wire 206 and bead 207 provide a handle or control section, it being noted that the handle section may be of other desired constructions. For example the handle section may be a control knob or an axially elongated, enlarged cylindrical portion fixedly joined to the proximal end of the core wire.

Even though the distal end portion 260 of the cable has been described as resiliently assuming a J-shape, it is to be understood that the distal end portion of the cable may be formed to resiliently assume a datum condition extending through an arcuate angle of about 35 to 45 degrees or arcuately between the 35 to 45 degrees and the J-shape when the core wire assembly is retracted.

In using the sixth embodiment of the guide wire, the guide wire with its J-portion in its generally straightened condition is inserted into a body vessel with one hand holding the proximal end of the cable of assembly 201 and the other hand holding the handle section M, N, 206, 207 of the assembly 200. When it is desired to turn the distal end portion of assembly 201, for example to enter a branch vessel that is not in a generally straight ahead direction, the core wire assembly is retracted (pulled rearwardly) in the direction of arrow 210 relative to the cable assembly 201 from the FIG. 12 position so that the flexible J-portion curves such that together with appropriate rotation of the cable assembly, the distal end will enter into the desired branch. After entering the branch vessels the core wire assembly is pushed opposite arrow 210 to straighten the J-portion.

In place of using one hand to operate the sixth embodiment of the guide wire, advantageously the guide wire handle assembly of this invention, generally designated 240 (FIG. 13), may be used. The handle assembly includes a proximal clamp portion 241, 246 that includes an axially elongated proximal member (main body member) 241 having a maximum diameter axially intermediate cylindrical portion 241a, an axially elongated, cylindrical distal portion 241b joined to portion 241a, an externally threaded portion 241c joined to the proximal end of portion 241a and a frustoconical portion 241d having its major base joined to the proximal end of portion 241c. A central bore 242 extends axially through the entire length of the proximal member 241.

Figure 14:
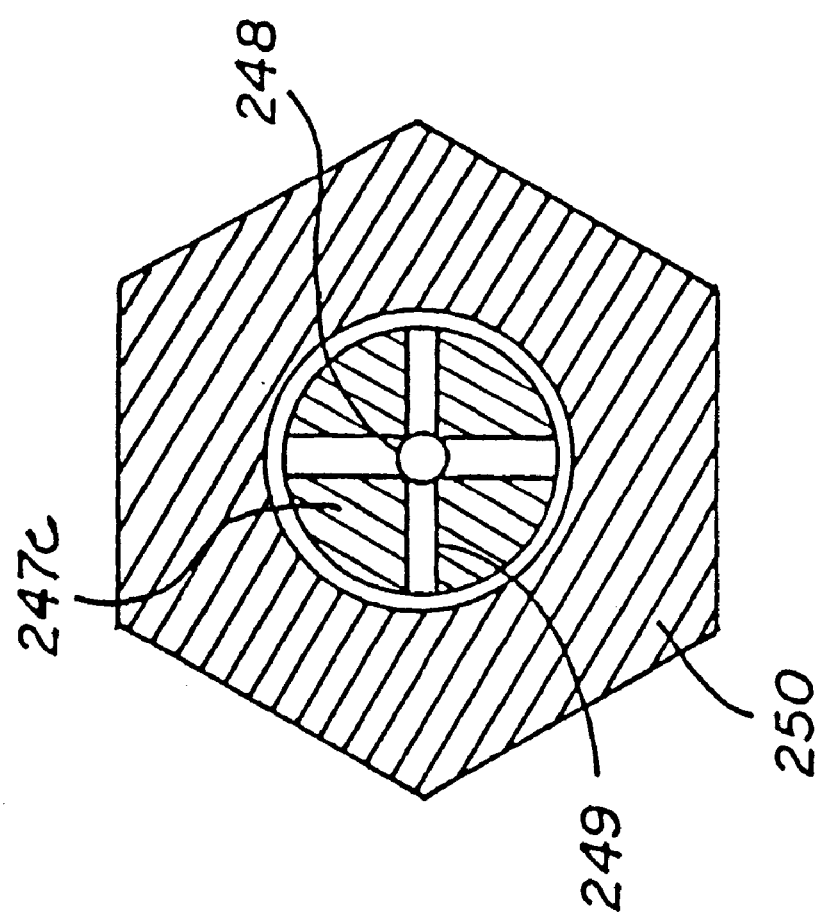
FIG. 14 is a transverse cross sectional view generally taken along the lines and in the direction of the arrows 14—14 other than the distal control member is sufficiently unthreaded that the distal clamp segments are in their datum unclamping position.

One or more slots 243 are provided in the frustoconical portion 241d to extend radially from the bore to the outer peripheral surface of portion 241c and may extend axially into the proximal part of the threaded portion to form at least one axially slotted segment. Advantageously there are provided 4 equally angularly spaced slots to provide four clamp segments such as shown in FIG. 14. At least the clamp segments are made of sufficient resiliency that they may be moved to a clamping position such as set forth below, but will resiliently return to their datum non-clamped position such as shown in FIG. 14 once the force that moved the segments to their clamped position is released.

To provide the force to move the proximal segments to their clamping positions, there is provided a proximal manually operated operative (clamp control) member 246. Desirably the clamp control is in a form of a cylindrical nut that has an outer circular peripheral surface that is knurled (the knurling not being shown). Further the control member has a distal threaded portion having internal threads 252 that form a matching fit with the threads of portion 241c and a wall surface portion defining a frustoconical bore (surface) portion 253 of an opposite taper from that of the radial outer surface of the frustoconical portion 241d. As a result, when threading the control member onto the clamp portion 241, the surface 253 initially engages the frustoconical portion 241d and thence forces the segments radially from their datum positions to their clamping position (datum position shown in FIG. 14 even though the control member is threaded to show them in their clamping position in FIG. 13).

The guide wire handle 240 also includes a distal clamp portion 247, 250 that has an axially elongated distal member (distal main body member) 247 having a maximum diameter proximal cylindrical end portion 247a, an externally threaded portion 247b having a maximum diameter less than that of portion 247a integrally joined to the distal end of portion 247a and a frustoconical portion portion 247c that has its major base integrally joined to the distal end of the threaded portion. Advantageously portion 247a is of the same outer diameter as that of portion 241a. The distal main body portion 247 has a central bore 248 (also see FIG. 14) extending axially therethrough. The bore 248 has a distal portion 248a that desirably is of the same diameter as bore 242, is coaxially aligned therewith, and extends axially through the frustoconical portion 247c. Advantageously bore portion 248a extends through the threaded portion 247b and into the proximal portion 247a. One or more slots 249 are provide in the main body portion 247 that advantageously extend at least the axial length of the frustoconical portion 247c to form at least one segment corresponding to those formed by slots 243. To force the segments of portion 247c to their clamping position there is provided a distal manually operated operative (clamp control) member 250 that may be in the form of a nut that is the same as the control member 246 and functions in the same manner as control member 246.

A screw 254 is threaded into the main body distal portion 241b and has its cylindrical head located in the axially elongated slot 255 that is formed in the main body proximal portion 247 to limit the axial movement of the proximal clamp member 241 relative to the distal clamp member 247. The length of the slot is such that the control member and proximal clamp portion 241 can be axially moved in the direction of arrow 210 from the solid line position of FIGS. 13, 15 to the dotted line position.

Figure 13:
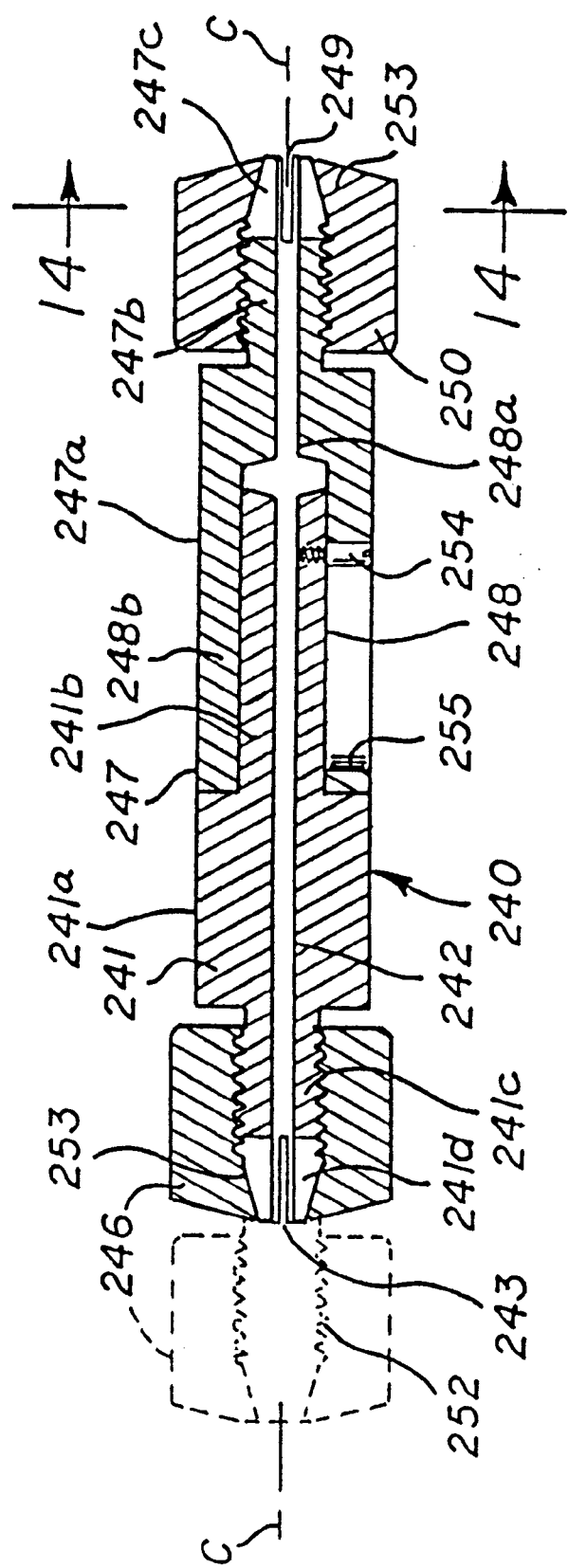
FIG. 13 is a cross sectional view of the handle of this invention that is shown in solid lines in its guide wire straightened position in solid lines and the handle proximate portion in the guide wire flexed position in dotted lines.

In using the sixth embodiment with the guide wire handle of FIG. 13, first the clamp control members 246, 250 are unthreaded sufficiently relative to the clamp main body portions 241, 247 respectively that the guide wire can be extended through the bore 242 and bore portion 248a. With the core wire assembly in its position relative to the cable assembly as shown in solid lines in FIGS. 15 and 13 and extended through the bore 242 and bore portion 248a such that the proximal terminal end of the cable assembly is closely adjacent to the proximal terminal end of the frustoconical portion 241d and screw (stop) 254 abutting against or very closely adjacent to the distal terminal end of slot 255, control member 246 is threaded onto the frustoconical portion 241d to force its segments to clampingly retain the core wire assembly in a fixed axial position relative to the proximal main body portion 241. At this time the proximal end of the cable assembly and the distal end of the core wire assembly are axially between the proximal and distal segments of the clamp main body portions respectively and the cable assembly proximal terminal end is more closely adjacent to the distal segments than the distal terminal end of core wire assembly handle section 205–207. Further the distal end member is threaded to force the distal segments to clampingly retain the cable M, N, in an axially fixed position relative to the main body distal portion 247.

Thereafter when the proximal control member is pulled to its dotted line position of FIG. 15 to pull the core wire out of the J-portion 260 whereby the J portion resiliently moves from its generally solid line position of FIG. 15 to its J-curved dotted line position of FIG. 15. Of course the amount of curvature of the J portion depends upon the axial movement of the proximal control member from its FIG. 15 solid line clamped position toward its dotted line position. The main body clamp portions 241 and 247 are made of materials (preferably plastic) and have the wall surface portions of the main body bore portion 248*b* and the outer cylindrical surface of portion 241*b* respectively to form a sufficiently close fit with one another that a manual force has to be applied to move the clamp main bodies 241, 247 relative to one another. Thus handle assembly 240 can be held by one hand as the guide wire is inserted into a body vessel, except when desiring to change the degree of curvature of the J portion. Additionally by using the cable M,N there is a substantially 1 to 1 transmittal of torque from the handle assembly to the distal end of the cable M,N, i.e. to bead 202.

Also the handle assembly is easily attachable and disattachable from the sixth embodiment of the guide wire; and if the handle section was a generally solid cylinder, the proximal end portion could be trimmed off in the event it extended proximally of the proximal control member when the clamp members are attached to operate the core wire relative to the coils as previously described. Further there are no protrusions, for example clamp screws, extending radially outwardly of the outer circumferential surfaces of members 241, 246, 247, 250.

Even though the handle assembly has been referred to as having distal and proximal portions, it is to be understood that the handle assembly can be rotated about an axis perpendicular to the central axis c—c whereby, for example, the distal portion becomes the proximal portion.

Figure 16:
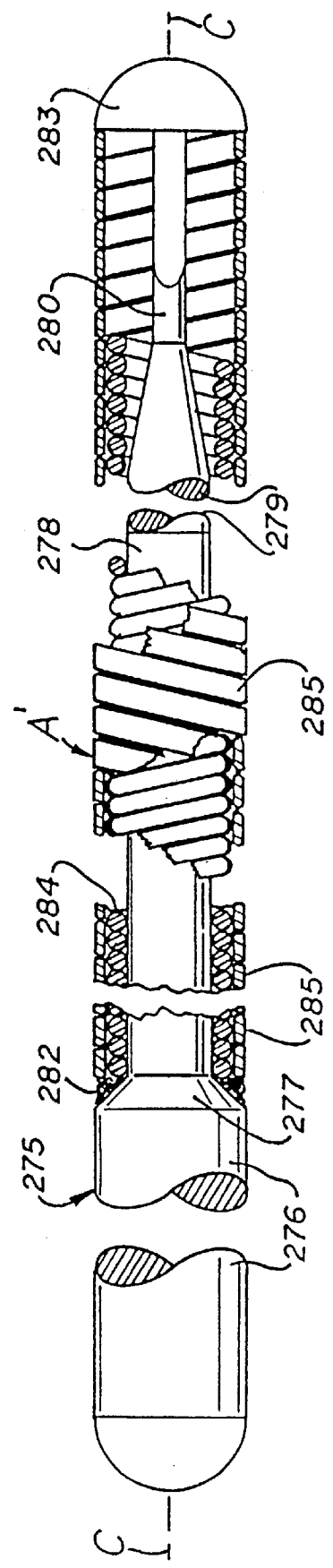
FIGS. 16–19 are cross sectional views of the seventh through eleventh embodiments of guide wires wherein a coil for at least a part of its axial length is in press fitting relationship to at least part of the axial length of the main wire, various portions of the coil(s) being shown in cross section and various portions of the axial length of the guide wires being broken away.
Figure 20:
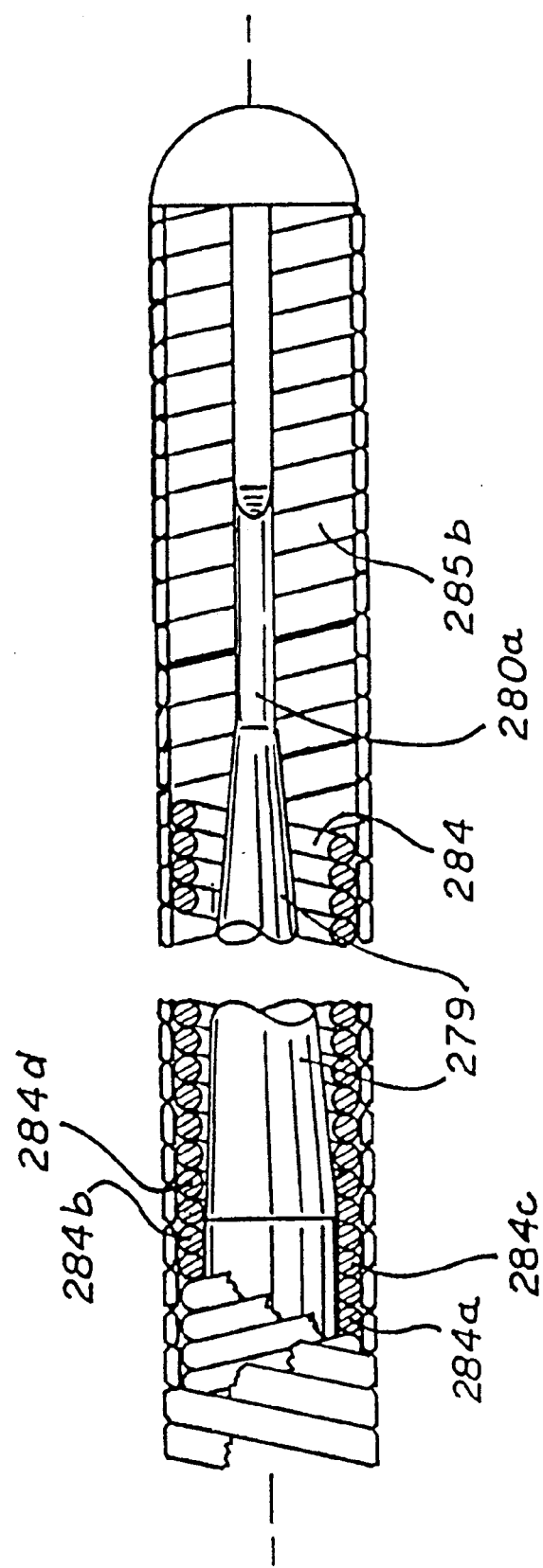
FIGS. 20–23 are enlarged views of the distal end portions of the guide wires shown in FIGS. 16–19 respectively.

Referring to FIGS. 16 and 20, the seventh embodiment of the invention, generally designated A', includes an axially elongated main (core) wire, generally designated 275, that has a proximal cylindrical portion 276, a short axial frustoconical portion 277 which has a major base integrally joined to the portion 276 and a minor base integrally joined to the proximal end of the intercylindrical portion 278, a distal frustoconical (tapered) portion 279 having its major base integrally joined to the intermediate portion 278 and a minor base integrally joined to the distal end portion 280. Advantageously the distal end portion has a cylindrical proximal part 280*a* and a flattened (generally rectangular in transverse cross section) distal part 280*b* that is joined to the distal tip (bead) 283. The intermediate portion 278 is of a substantially smaller diameter than that of the proximal portion 276 and of a substantially larger transverse cross sectional area than the corresponding area of the distal end portion.

The guide wire portions 278, 279 extend within the inner coil 284 while the inner coil is in interference fitting relationship with the outer coil 285. The proximal ends of the inner and outer coils are adjacent to the frustoconical portion 277 and secured thereto by brazing or solder 282 while the distal end of the outer coil is joined to the guide wire tip. The inner coil is of a shorter length than the outer coil whereby its distal end terminates axially adjacent to the juncture of the distal tapered core end portions 279, 280 and radially spaced therefrom.

In making the guide wire A', the inner coil is wound to, in its relaxed condition, have a smaller inner diameter than the diameter of the intermediate cylindrical portion 278 (for example by two or three thousandths of an inch) but of a larger diameter than the distal end portion 280. The outer coil is wound to have a smaller inner diameter in its relaxed condition than the outer diameter of the inner coil in its relaxed condition. Preferably each of the coils is multifilar. That is each of the coils are wound such as described with reference to coils M, N.

An unwinding force is applied to the opposite ends of the inner coil to sufficiently unwind it to have an inner diameter larger than the diameter of the intermediate cylindrical portion and thence the main wire distal end portion is moved into and through the partially unwound coil until the proximal terminal end of the inner coil abuts against or is very closely adjacent to the proximal frustoconical portion. Thereafter the unwinding force is removed and the inner coil contracts to form a press fit with the intermediate cylindrical portion throughout its radially adjacent axial length. As a result the inner coil forms a press fit with the intermediate cylindrical portion 278 and a very small axial part of the tapered portion 279 (the amount depending upon the degree of taper and the inner diameter of the coil in its relaxed condition relative to the diameter of portion 278).

Next the outer coil is partially unwound and thence the inner coil is inserted into the outer coil such as previously described with reference to inserting coil M into coil N to have the proximal end of the outer coil abut against or axially closely adjacent to the frustroconical portion 277, and thence the outer coil is allowed to resiliently contract to form an interference fit with the inner coil throughout the axial length of the inner coil. The tip 283 is subsequently formed to be joined to the distal end of the outer coil and the distal end portion 280. The outer coil outer diameter is substantially the same as the diameter of the proximal end portion 276. Due to the inner coil being in press fitting relationship to the cylinder portion 278 and the outer coil being in interference fitting relationship to the inner coil, a substantially 1 to 1 torque transmission from the wire proximal terminal end part of the proximal end portion to the coil distal end portion is achieved without any soldering, brazing or similar manner of attaching the inner coil to the main wire. However to provide a smooth transition from the proximal cylinder end portion 276 to the coils' proximal ends, the proximal ends of the coils are brazed or similarly joined to the main wire at 282 whereby the guide wire is of a substantially constant outer diameter from the rounded terminal part of portion 276 to the bead 283. There is an annular clearance space between the inner spring coil and the main wire that extends from the tip 283 to axially closely adjacent to the juncture of the tapered portion 279 to the intermediate cylindrical portion 278.

Figure 17:
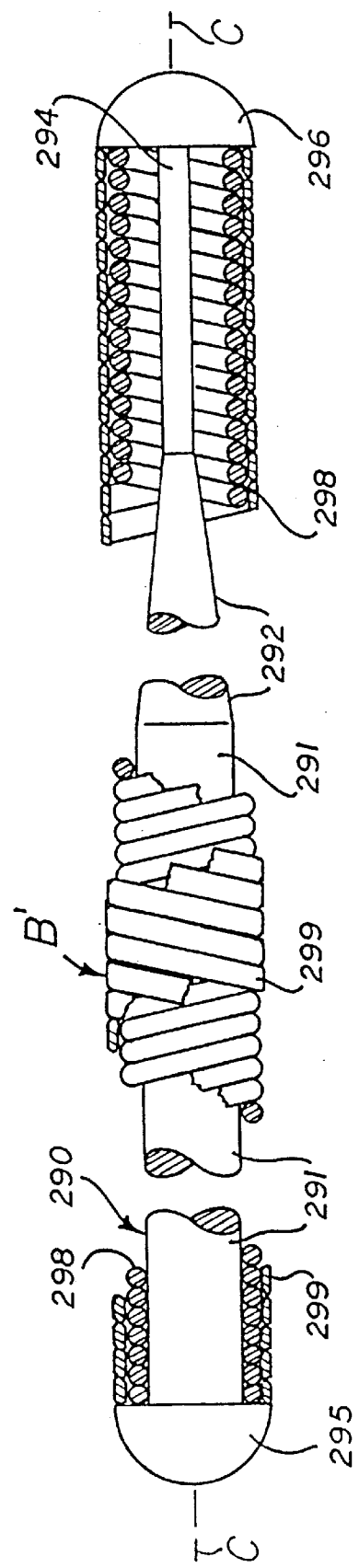
Figure 21:
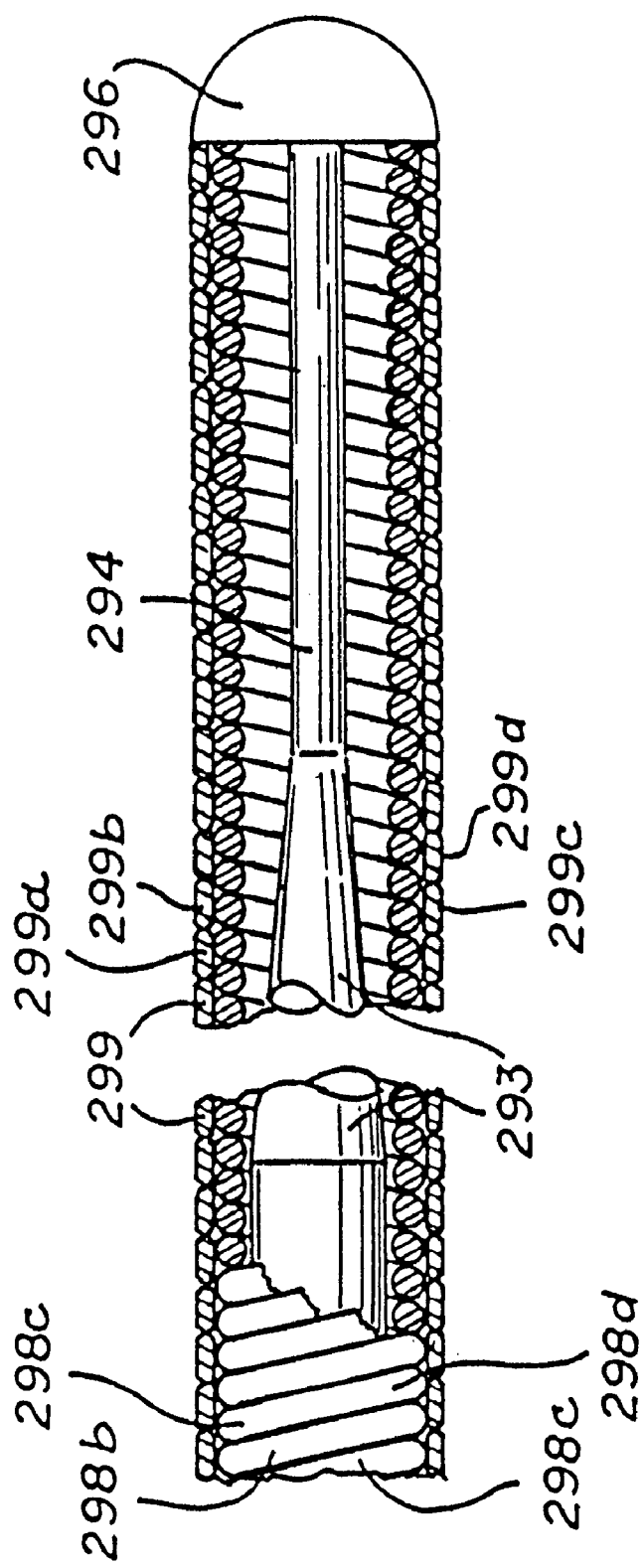

Referring to FIGS. 17 and 21, the eight embodiment of the guide wire of this invention, generally designated B' includes an axially elongated main wire (core wire), generally designated 290, that has a proximal cylindrical portion 291 and a frustoconical (tapered) portion 292 that has its major base (proximal end) joined to portion 291 and its minor base (distal end) joined to the wire distal end portion 294. The cylindrical portion 291 is of a substantially larger diameter than that of the distal end portion. The proximal end of the cylindrical portion 291 is joined to the proximal tip (bead) 295 while the distal end of the distal end portion 294 is joined to the distal tip (bead) 296.

The inner coil 298 is of an axial length to extend axially between and abut against the tips. Further the inner spring coil is in press fitting relationship with the axial length of the proximal cylindrical portion 291 and is radially spaced from nearly the entire length of the tapered portion and from the entire length of the distal end portion 294 to provide an annular clearance space extending axially from the distal tip to axially adjacent to the juncture of the tapered portion to the proximal cylindrical portion. Additionally there is provided an outer spring coil 299 that is of a substantially constant outer diameter and in interference fitting relationship to the inner coil and extends the axial length thereof. The method of mounting the inner and outer coils on the main wire is the same as that described with reference to the seventh embodiment other than both coils extend the axial length of the main wire, the bead 296 being formed to join to the distal terminal end parts of the coils and the distal end portion 294 to one another after the main wire is extended into the coils and brazing may be provided at the terminal proximal ends of the coils and the main wire.

The outer diameter of the outer spring coil is substantially the same as the maximum transverse diameter of each of the proximal and distal tips.

At times it is desired to have a guide wire of a given outer diameter from one end to the other and have very good torque transmission from one end to the other while at the same time having the appropriate balance between stiffness and flexibility over the different parts of the axial length thereof. As to the seventh and eighth embodiments, if the intermediate portion 278 and proximal portion 291 were of the inner diameter of respective outer coil so as to eliminate the inner coil, the resulting guide wire would be stiffer than desired along the lengths of portions 278, 291. Similarly if the portions 278, 291 were not modified as set forth above, but rather the radial dimension of the outer coils were increased to be of the combined radial dimensions of the inner and outer coils, the desired flexiblity would not be achieved. However by providing the inner coil to serve as a filler coil that substantially fills the annular space between the portions 278, 291 and the outer spring coils, both the desired degree of flexibility and outer diameter of the guide wire is obtained.

With further reference to the eighth embodiment, by using a single filar inner coil and a multifilar outer coil, greater flexibility is obtained than if both of the inner and outer coils are multifilar. Also the eighth embodiment may be made with the inner coil multifilar and the outer coil single filar.

Figure 18:
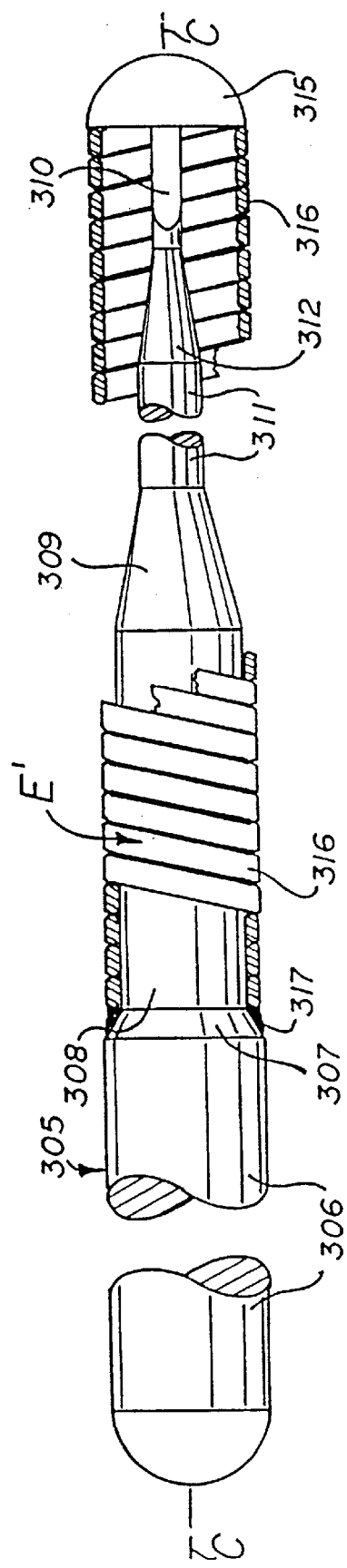
Figure 22:
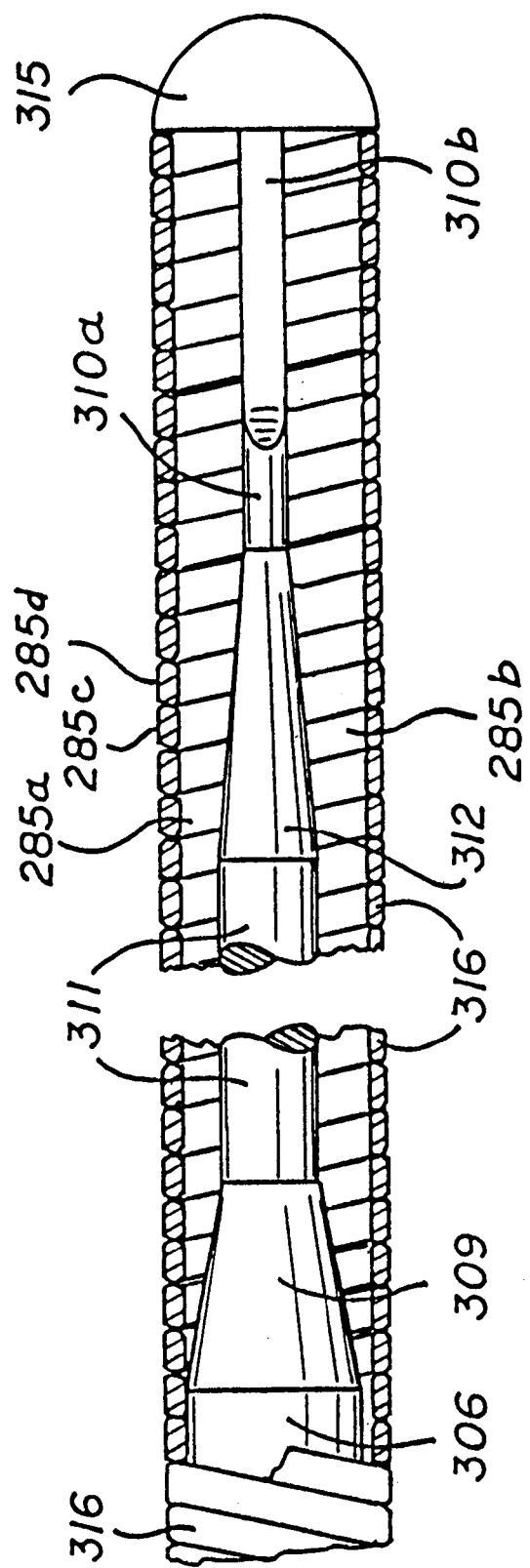

Referring to FIGS. 18 and 22, the ninth embodiment of the guide wire of the invention, generally designated E', includes a main wire, generally designated 305. The main wire 305 is substantially the same in shape as main wire 275 other than for the relative diameters of their proximal and intermediate cylindrical portions. That is, the main wire 305 includes a proximal cylindrical portion 306, a frustoconical portion 307, an intermediate cylindrical portion 308, an intermediate frustoconical portion 309, as intermediate cylindrical portion 311 and a distal portion 310 that has a cylindrical part 310a and a distal flattened part 310b.

A coil 316 that in its relaxed condition is of an inner diameter that is less than the diameter of the intermediate cylindrical portion 308 is partially unwound and retained to have a larger inner diameter than portion 308 while the main wire, other than the proximal cylindrical portion 306, is extended into the coil. Thence the force retaining the coil in its partially unwound condition is released whereby the coil contracts to form a press fit with the intermediate cylindrical portion 308 and the proximal terminal end of the coil closely adjacent to or in abutting relationship to frustoconical portion 307. Brazing 317 is provided to fill the gap between the proximal end of the coil and the proximal cylindrical portion and provide a smooth transition from the coil to the proximal cylindrical portion, i.e. the brazing having substantially the same outer diameter as the the outer diameter of the part of the coil on the intermediate cylindrical portion and the diameter of the proximal cylindrical portion.

A distal tip (bead) 315 is joined to the distal terminal end of the coil and the distal end portion 310 after the coil is positioned on the main wire and the coil has contracted. The distal tip has a maximum transverse diameter substantially the same as the outer diameter of the distal end of the coil and the portion 306.

The difference in diameters of the proximal and intermediate cylindrical portions 306, 308 is less than that of the difference in the diameters of portions 276, 278 and accordingly the ninth embodiment includes a single coil. As with the seventh embodiment, the ninth embodiment has an annular clearance space radially between the inner peripheral wall of the coil 316 and the main wire from the tip 315 to closely adjacent to the juncture of the intermediate cylindrical portion 308 to the intermediate frustoconical portion 309.

Figure 19:
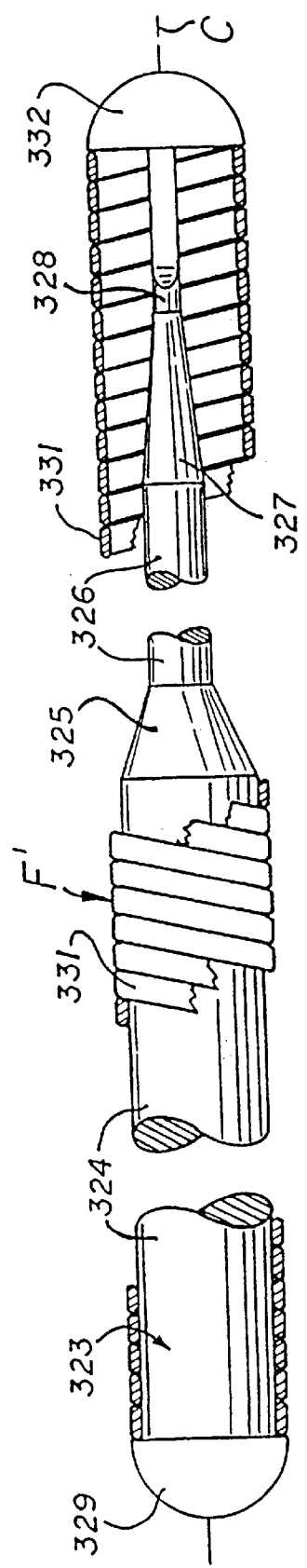
Figure 23:
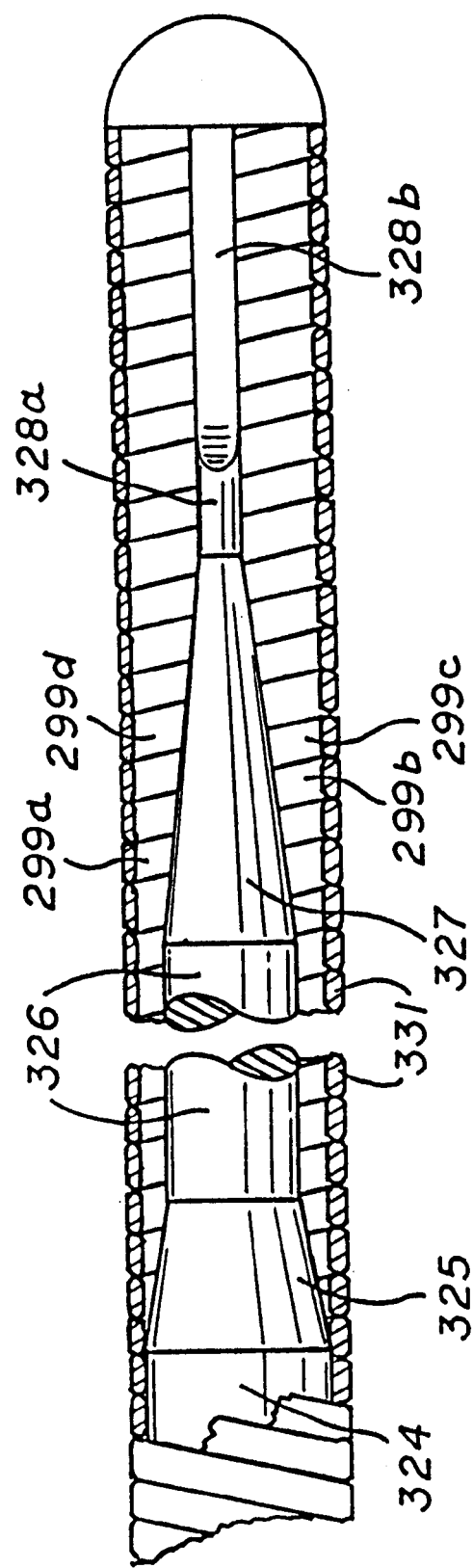

Referring to FIGS. 19 and 23, the tenth embodiment of the invention, generally designated F', includes a main wire, generally designated 323 that includes a proximal cylindrical portion 324 joined to the major base of the proximal frustoconical (tapered) portion 325 which has its minor base joined to the intermediate cylindrical portion 326. The intermediate cylindrical portion 326 is joined to the major base of the distal tapered portion 327 while its minor base is joined to the distal end portion 328. Portion 328 has a proximal cylindrical part 328a and a distal flattened portion 328b.

The proximal end of the cylindrical portion 324 is joined to a proximal (bead) tip 329 which has a maximum transverse diameter adjacent to and of a larger diameter than portion 325. A spring coil 331 in its relaxed condition has an inner diameter smaller than the diameter of the proximal cylindrical portion but larger than the diameter of the intermediate cylindrical portion 326 is partially unwound such as described relative to the FIGS. 16–18 embodiments, the main wire extended into the coil to have the proximal tip abut against the proximal terminal end of the coil and thence the coil allowed to contract to form a press fit with the proximal cylindrical portion 324 throughout the axial length thereof. A distal tip (bead) 332 is joined to the distal terminal ends of the coil and the flattened portion 328a. An annular clearance space is provided radially between the main wire and the inner peripheral wall of the coil axially from the distal tip to adjacent to the juncture of the proximal tapered portion to the proximal cylindrical portion.

Even though the sixth embodiment has been described and shown with reference to the core wire 208 having its cylindrical portion 208a being of a constant diameter, as may be seen from the twelfth embodiment (FIGS. 29 and 30), the distal part of the core wire portion 208a may be modified to be tapered. That is in the twelfth embodiment, generally designated 500, the core wire 508 has a constant diameter cylindrical portion 508a that extends axially away from the core wire proximal bead or handle (not shown but corresponds to bead 207), an axially intermediate tapered portion 508b having its major base joined to the distal end of portion 508a, and a distal terminal spherical bead (tip)

portion 508d joined to the distal end of portion 508b. For most uses the axial length of wire portion 508a is several times greater than the combination of the axial lengths of portions 508b and 508d. When the core wire assembly having the core wire 508 is extended within the cable assembly 201, the core wire in entering into the distal part of the cable assembly will move the J-shaped portion from its datum condition to decrease the angle of curvature thereto, and when the bead 508d is closely adjacent to the distal tip 202, the J-portion 260 will extend through an arcuate angle, for example, about 25 to 30 degrees.

The curvature of the J-portion 260 with the distal part 508b and 508d of the core wore in its extended position results from the greater flexibility thereof than the distal part of core wire portion 208a extending the same distance into the cable M, N. That is, due to the resiliency of the J-portion 260 constantly urging portion 260 to assume a J-shape results in the distal part 508b and 508d being arcuately curved even with the core wire 508 in its extended position; however the arcuate angle that portion 260 extends through is substantially less than when the wire 508 has been completely retracted out of the J-portion 260.

In the event that the portion 260 is modified to in its datum position arcuately extend through an angle of about 35 to 45 degrees when the core wire is not extended thereinto, than when the core wire 508 is moved to its extended position, the arcuate angle that portion 260 extends through is of a substantially smaller arcuate angle than that indicated in solid lines in FIG. 30, but is still arcuately curved. Thus, with reference to the twelfth embodiment the amount of curvature of the portion 260 with the core wire in its fully extended position depends in part on the angle of arcuate curvature portion 260 resiliently assumes when the core wire is entirely out of portion 260, the angle being substantially less with the core wire 508 in its extended position than in its retracted position.

Even though it has been set forth that the datum angle of curvature of the portion 260 is J-shaped or about 35 to 45 degrees, it is to be understood that the arcuate angle that the distal portion of the cable assembly extends through in its datum condition may be varied to be other than that set forth. Further, with reference to each of the sixth and twelfth embodiments of the guide wire, due to the provision of both inner and outer coils M, N together with the coils being in interference fitting relationship such as described herein, even when the distal end portion of the cable coils are in a generally J-shaped configuration, there is not a sufficiently large space for either of the distal tip 208d, or tip 508d to extend outwardly between adjacent helices of both of the coils M, N to injure a vascular vessel during use. Such an outward extension of the core wire distal bead is blocked by one or both of the coils, but with the distal part of the core as modified in accordance with the twelfth embodiment, the core wire distal part is more flexible than the core wire illustrated in FIG. 12 (assuming that the core wire portion 508a was of the same diameter as portion 208a).

Figure 11:
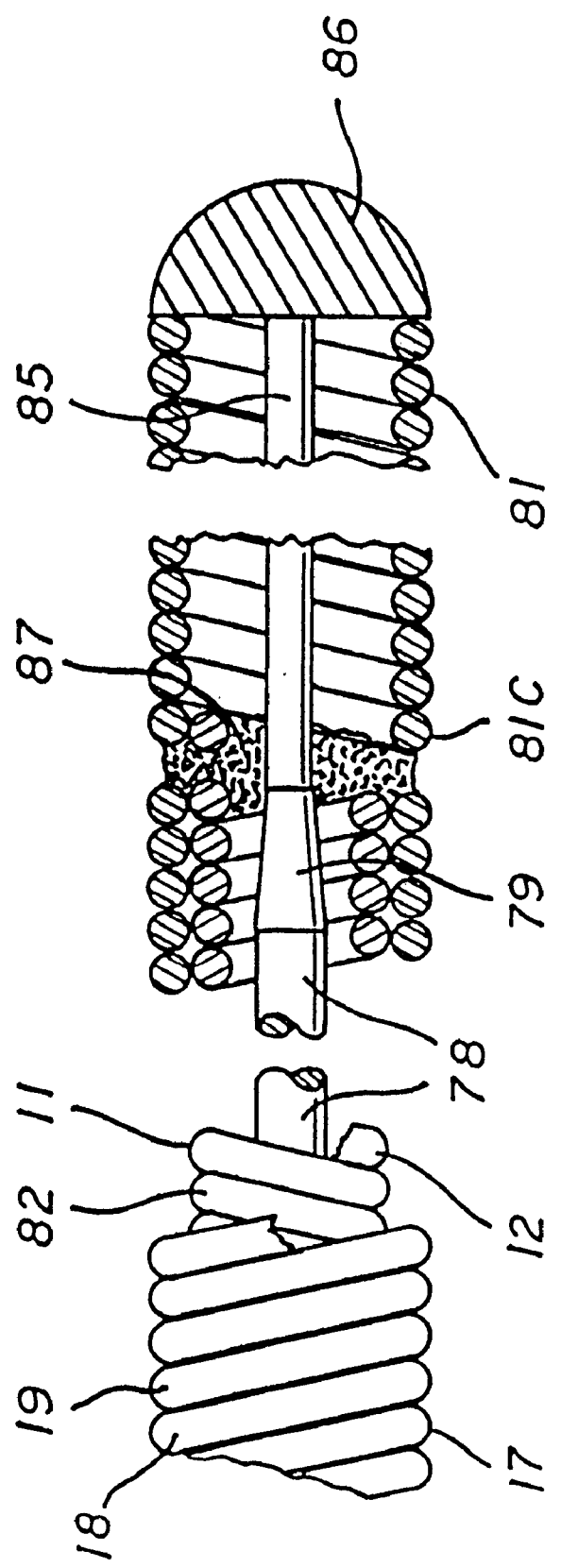

Better performance is obtained with the embodiments of FIGS. 18 and 19 than with the embodiments of FIGS. 10 and 11 in that the brazing 87 and other guide wires having similar brazed areas axially between the distal bead and the main wire proximal end portion precludes there being a smooth transition of flexibility from axially proximally of the brazing to distally of the brazing. Further, particularly with the coils 284, 285, 298, 299 being multifilar and of substantially constant outer diameters from one end to the other, there is very good transmission of torque even without the inclusion of a joint such as brazing 87.

Preferably each of the coils of embodiments 16–19 are multifilar, for example 4 individual wires wound with adjacent helices in axial abutting relationship. For example coils 285, 316 are made from wires 285a, 285b, 285c, 285d; coils 299, 331 are made of wires 299a, 299b, 299c, 299d and each of coils 284 and 298 are made of wires 284a, 284b, 284c, 284d and 298a, 298b, 298c 298d respectively.

With reference to the embodiments of FIGS. 16–19, they each have stiffness and flexibility characteristics that are different from one another and thus the one used depends upon the particular situation where one is to be used.

The wires forming the coils of FIGS. 16–23 may be round, rectangular or of other suitable transverse cross sectional shapes. Further if more than one coil is provided in radial abutting relationship, it is more desirable to have coil wires of one coil of, for example round or rectangular shapes in interference fitting relation to round wires over one coil of rectangular wire in interference fitting relationship to a second coil of rectangular coil wires.

With reference to each of the guide wires of FIGS. 16–19, normally the axial length of the proximal cylindrical portions 276, 291, 306, 324 is several times greater than the remainder of the axial length of the respective guide wire. Additionally, the axial length of the intermediate cylindrical portions 291, 308 is many times greater than the axial length of the remainder of the main wire that extends distally thereof. As a result the axial length of the respective main wire that a coil is in press fitting relationship with is many times greater than the axial distance from the distal end of the press fitting relationship to the distal tip. Additionally since usually at least each of the coils in press fitting relationship with the main wire is multifilar with axially adjacent helices in abutting relationship, there is a substantially 1 to 1 transfer of torque from the guide wire proximal end portion to the distal tip and accordingly no substantial twisting of the smallest transverse dimensional distal end portions 280, 294, 310, 328 of the guide wires.

As an example of the invention, but not otherwise as a limitation thereon, the axial length of the guide wire may be 100–275 cm. For example with the axial length being 181 cm., the proximal cylindrical portions 276, 299, 306, 323 may be about 150 cm., cylindrical portions 278, 308 may be about 25 cm., and the distal end portions 280, 294, 310, 328 about 1 cm. to 2 cm., and preferably the maximum diameter to the guide wire is less than about 1/16".

A further use that may be made of the cable is to have electric leads (not shown) extended through the cable lumen or to be used in place of each of the coil springs such as disclosed in U.S. Pat. No. 4,154,247. Still another use is that fiber optical bundle (light guide), not shown, may be located in the hollow lumen of the cable 10 in a fixed relationship to the cable, or may be pushed into the cable after the cable has been moved to the desired location in a body vessel. Another use is to incorporate the cable 10 as part of a catheter wherein the cable is embedded in or surrounded by a plastic sheath (not shown) which is in fixed axial relationship to the cable. For example the cable may be used in place of the coil spring in a catheter such as disclosed by U.S. Pat. No. 3,757,768 to Kline.

As one example of a catheter of this invention, the first embodiment, generally designated 100 (see FIG. 24) includes an inner metal coil M, an outer metal coil N with the coils being formed and mounted in the same manner as described with reference to FIGS. 1–3, a Luer connector or fitting, generally designated 101 that includes a reduced diameter distal end portion 102 that has a distal, annular terminal edge 103, an axial intermediate, intermediate diameter portion 104 joined to portion 102 to form an annular shoulder 105 and a proximal end portion 106 that may be of a shape to provide a male or female connection, depending upon the Luer connector used. Advantageously the proximal ends of the inner and outer coils abut against or are located very closely adjacent to the shoulder 105 and the proximal end portions of the coils are brazed or otherwise suitably fixedly attached to one or both of the fitting portions 102, 104. The fitting bore 110 at least through portion 102 may be of the same diameter as the inner diameter of the inner tubular portion 107.

Within the inner coil there is provided a plastic inner sleeve (tubular portion) 107 having a proximal end abutting against and/or joined to fitting end 103 and extending axially adjacent to or a short distance axially more remote from the fitting than the distal ends of the coils. Further there is provided a plastic outer sleeve (tubular portion) 108 that has a proximal end portion that advantageously extends over fitting portion 104 and secured thereto and a distal end portion that extends distally beyond the coils, tapered and joined to the sleeve 107 to form a catheter tip 108a. The tip may have a distal axial outlet opening 107a such as shown, or alternately may be closed at its distal end and have a radial outlet opening (not shown) a short distance from the terminal distal end of the tip.

Figure 24:
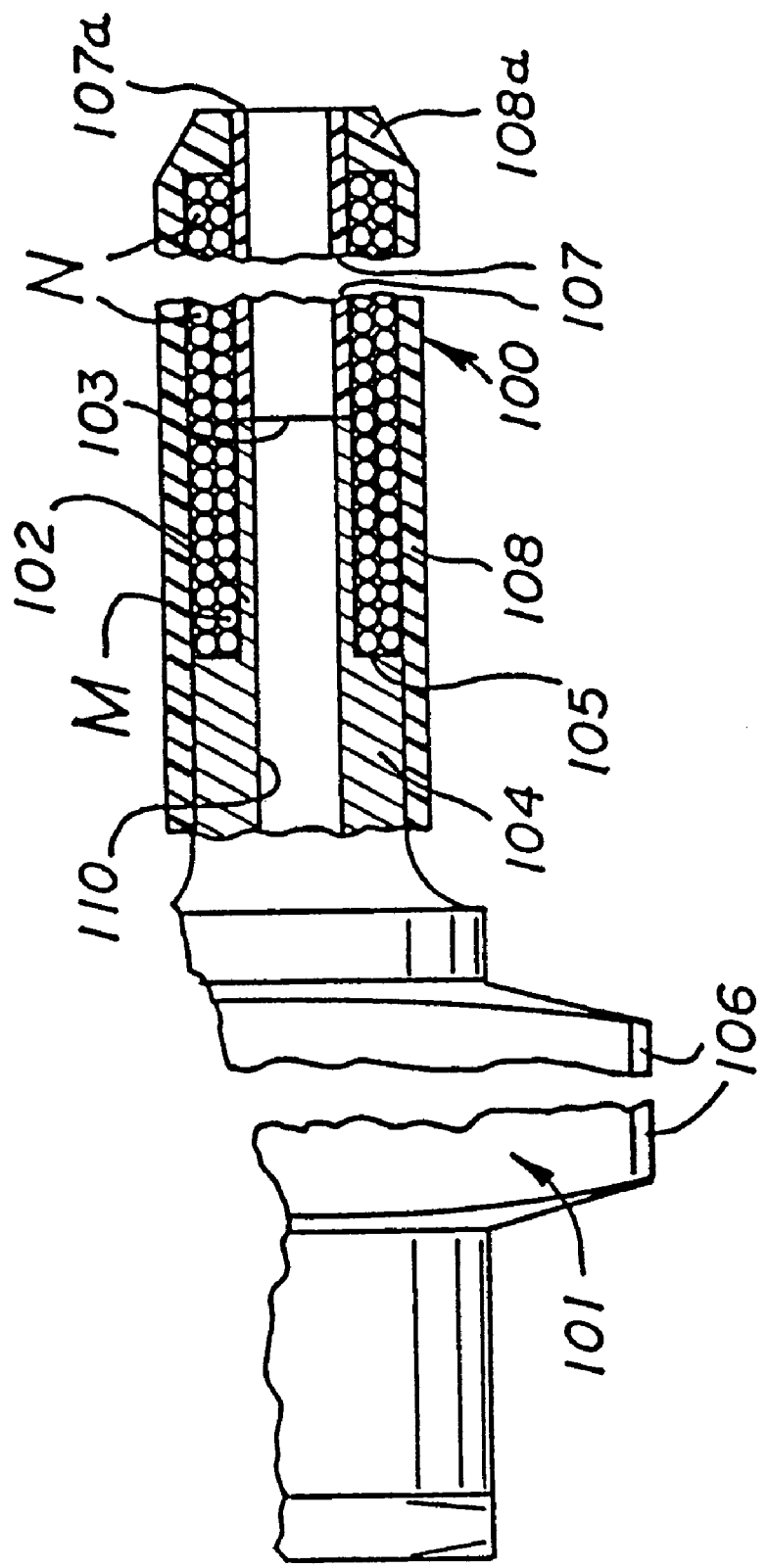
FIG. 24 is a fragmentary view, part in cross section of the first embodiment of the catheter of this invention with the axial intermediate portions broken away.
Figure 25:
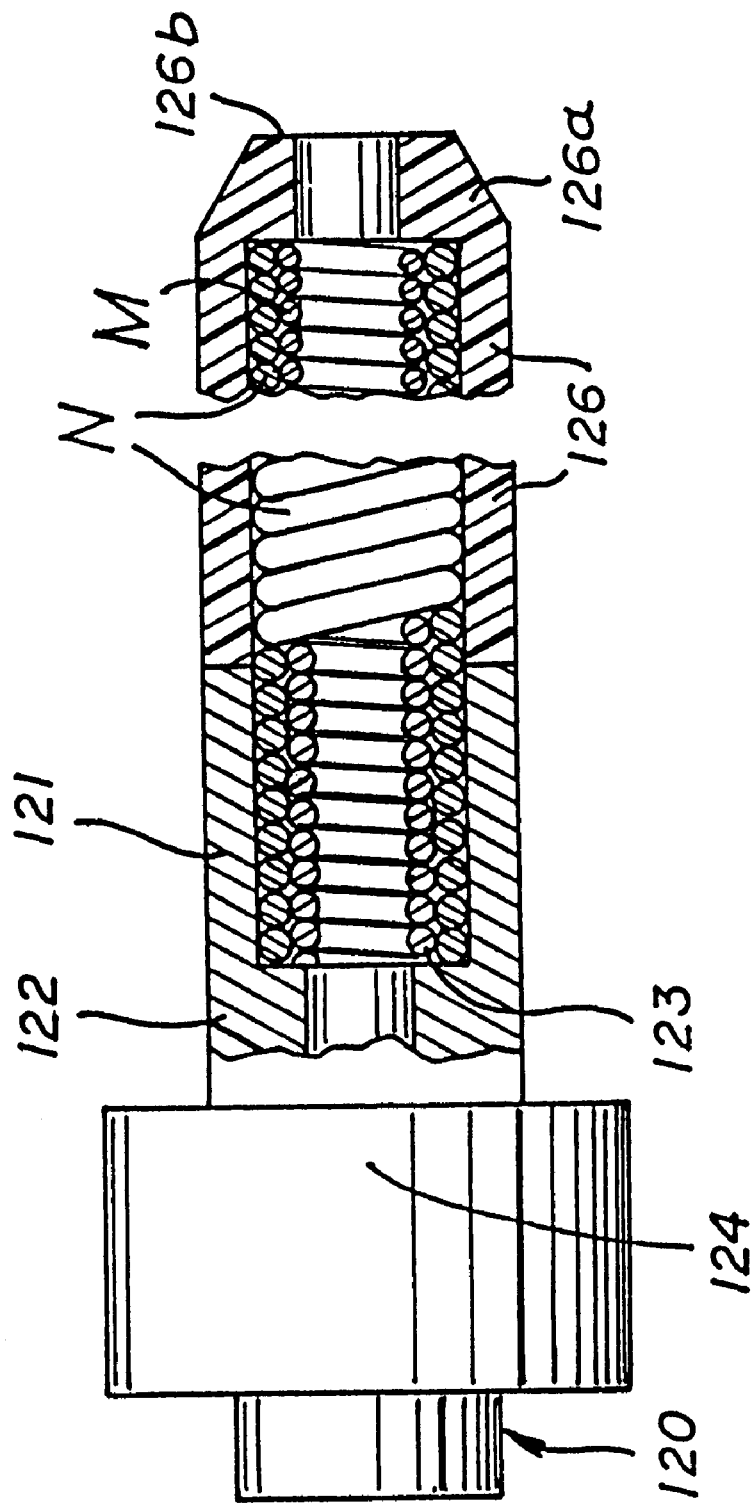
FIG. 25 is a fragmentary view, part in cross section of the second embodiment of the catheter of this invention with the axial intermediate portions broken away.

Referring to FIG. 25, the second embodiment of the catheter of this invention, generally designated 120, includes inner and outer coils M, N that are the same as the embodiment of FIG. 24, a Luer connector (fitting) having a distal end portion 121, an axial intermediate portion 122 that has a smaller inner diameter than the distal portion 121 and at its juncture to portion 121 forms an annular shoulder 123 and a proximal portion 124 suitably shaped to form the desired one of a female or male connector, and an outer sleeve (tubular portion) 126 that has a proximal end abutting against and/or joined to the terminal end of the fitting distal portion. The outer sleeve advantageously has a tapered tip end portion 126a to extend distally away from the distal end portion of the cable, and if the tip has a terminal axial outlet opening 126b, the inner diameters of the tip, the inner coil and the fitting distal portion may be substantially the same. The proximal end portions of the coils are brazed to fitting portion 121.

Figure 26:
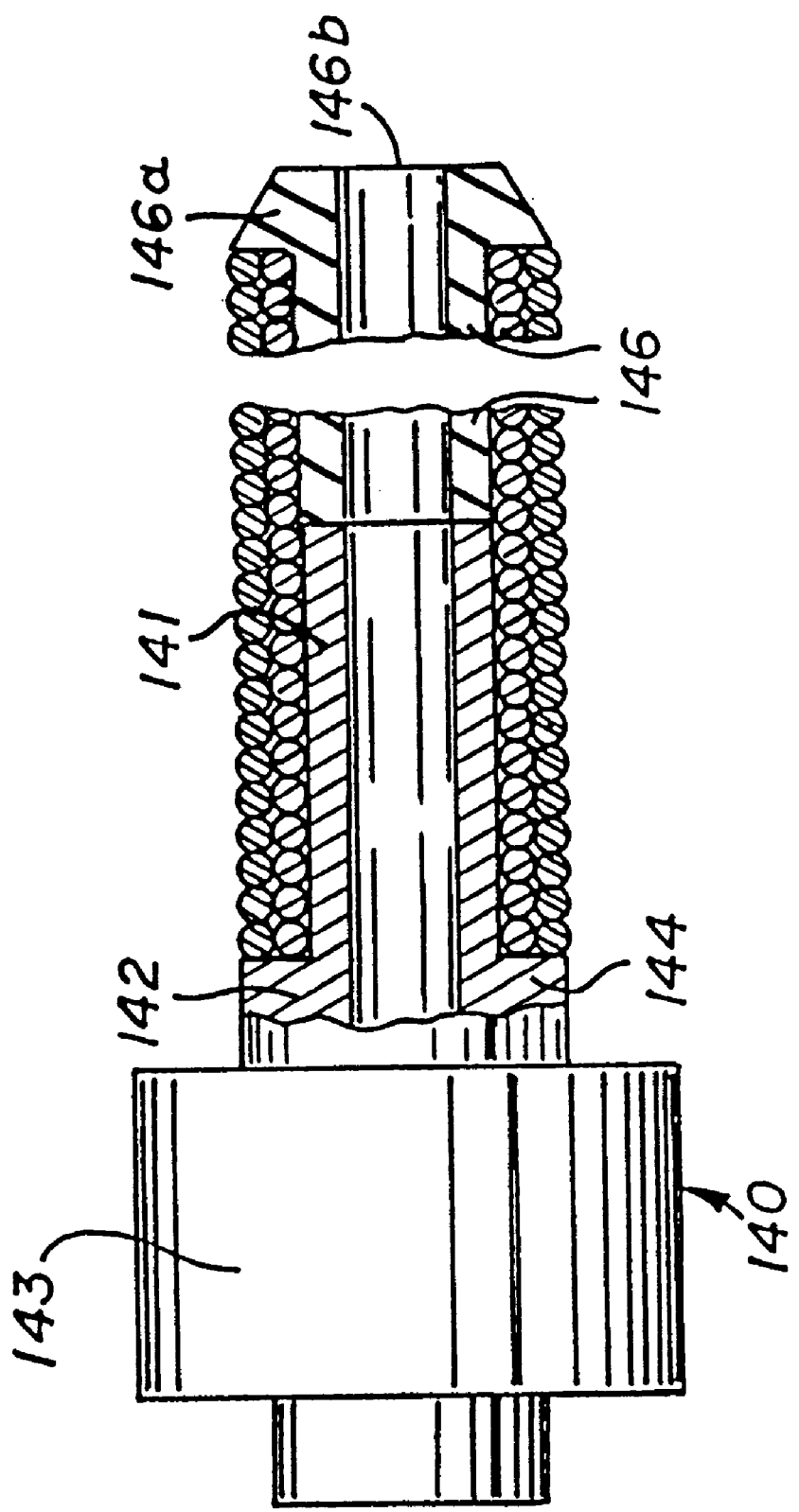
FIG. 26 is a fragmentary view, part in cross section of the third embodiment of the catheter of this invention with the axial intermediate portion broken away.

Referring to FIG. 26, the third embodiment of the catheter of this invention, generally designated 140, includes a Luer connector (fitting) that has distal, axial intermediate and proximal portions 141, 142 and 143 that as illustrated has portion 143 of a different construction from that of fitting 101, but may be the same. The juncture of portions 141, 142 form an annular shoulder 144. The proximal end portion of the inner and outer coils M, N extend over fitting portion 141 to be adjacent to or abut against the shoulder 144 and are brazed to distal portion 141 and to one another. An inner sleeve (tubular portion) 146 is provided within the inner coil to have its outer peripheral surface abut against the inner peripheral wall of the inner coil, has its proximal end abut against or adjacent to the distal terminal end of portion 141 and has an outer diameter about the same as that of portion 141, other than for the distal tip 146a. The tip at its proximal end is joined to the distal end of the cable M, N and is of an outer diameter substantially the same as that of the outer coil. The outer diameter of the outer coil advantageously is substantially the same as that of fitting portion 142. The tip shown has an axial outlet 146b and extends axially more remote from the fitting than the coils and has an inner diameter that advantageously may be same as the inner diameter of fitting portion 141.

Figure 27:
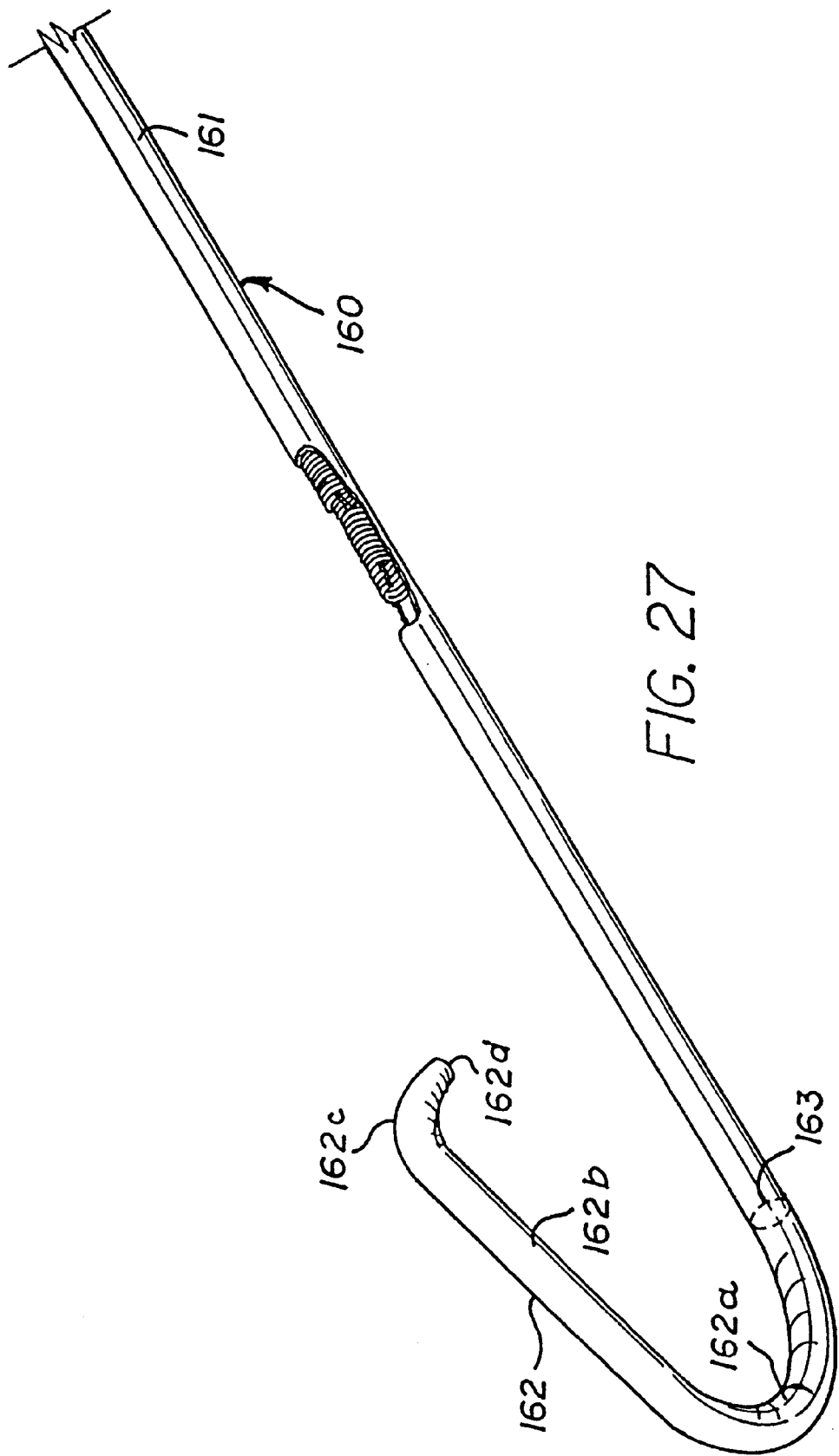
FIG. 27 is a perspective view of the distal end portion of a left coronary guide catheter that incorporates the cable of this invention with part of the plastic outer tubular portion and various parts of the cable broken away.
Figure 28:
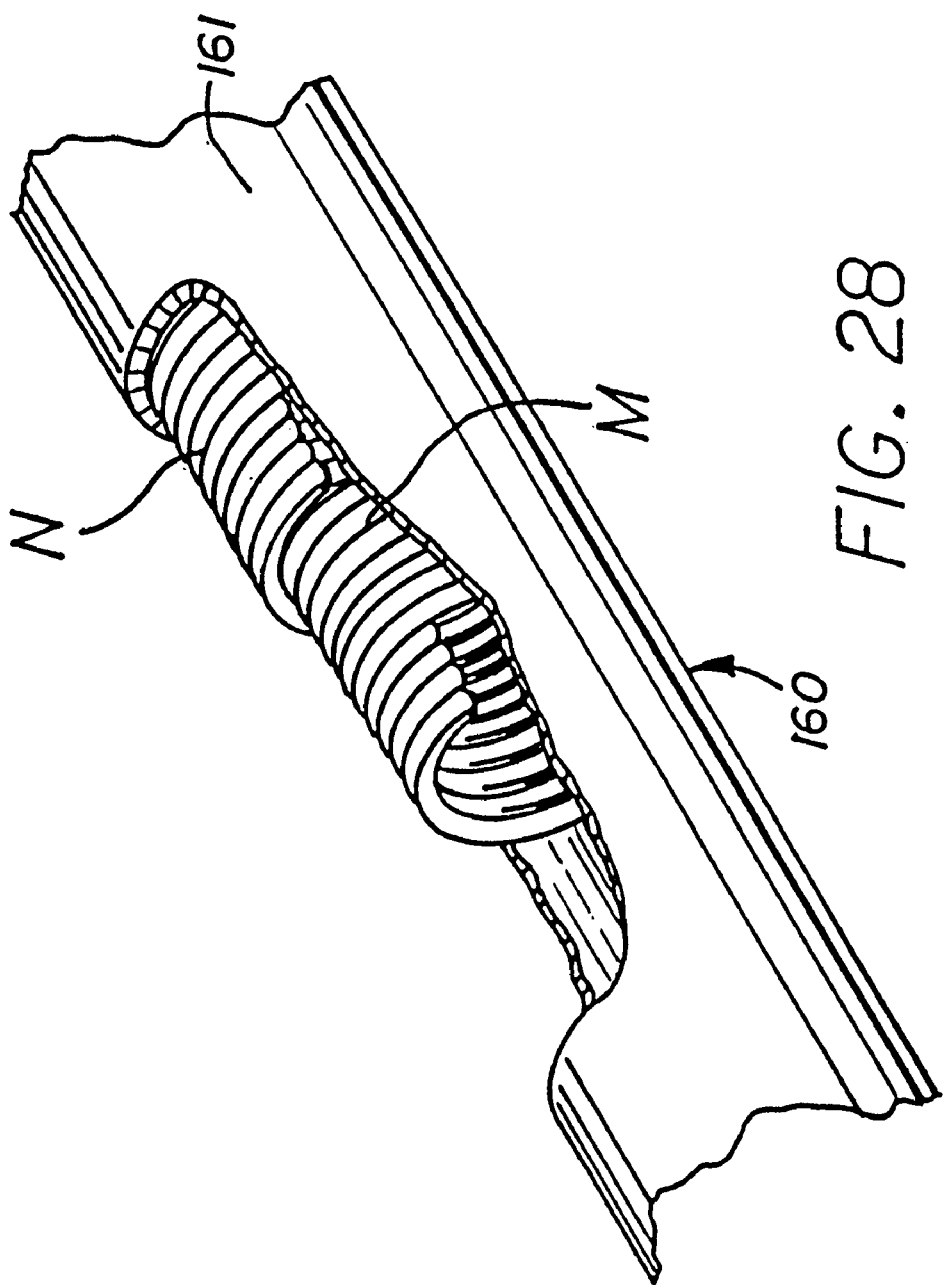
FIG. 28 is a showing of a part of the structure shown in FIG. 27 other than being on a larger scale.

Referring to FIGS. 27 and 28, the fourth embodiment of the catheter of the invention, generally designated 160, may be the same as the embodiment of FIG. 25 other than for its distal end portion. That is catheter 160 has an outer sleeve (tubular portion) 161, 162 having a predominately linear (may be slightly curved) axially intermediate portion 161 (only the distal part of the portion 161 being shown) that extends the major part of the total length of the catheter, a proximal end portion coaxial with a portion of a fitting (not shown) and a distal end portion 162 that may be of different curvatures, depending upon the usage that is to be made of the catheter. For example if the catheter is to be used as a left coronary angioplasty guide catheter, then the distal end portion of the cable M, N terminates at 163 which is closely adjacent to the juncture of sleeve portion 161 to portion 162. That is the sleeve distal end portion has a reversely curved part 162a that at one end is joined to portion 161, a relatively short, nearly linear part 162b that at one end is joined to the opposite end of part 162a, and a relatively short, sharply curved part 162c that at one end is joined to the opposite end of part 162b and has a terminal tapered tip end part 162d. If the catheter is to be used for other than a left coronary, the sleeve distal end portion would be of a shape different from that shown in FIG. 27. Although the embodiment of FIG. 27 does not have an inner sleeve, it could be provided with an inner sleeve that has its distal end extending a slight distance distally beyond the distal terminal end of the cable and is joined to the outer sleeve.

With each of the embodiments of the catheters of this invention, the distal terminal end parts of each of the strands of wires of the inner and outer coils are fixedly joined to one another, for example by brazing. Further the proximal end parts of each of the strands of wire of the inner and outer coils are fixedly joined to one another and to the distal end portion of the fitting, for example by a brazing step. If the fitting is plastic, the proximal end parts of the coils may be fixed to the fitting by, for example, a suitable epoxy compound.

The shape of the catheter fitting may be varied as long as the cable is fixed to the fitting, and preferably the inner diameter of the fitting distal end portion is substantially the same as that of the inner tube portion, if provided, and if not, the inner diameter of the inner coil. For example with reference to FIG. 24, fitting portion 104 may be of an outer diameter substantially the same as that of the outer tubular portion 108 and the proximal end of the outer tubular portion terminate at the juncture of portions 102, 104.

The catheter may be in part formed in different manners. For example with reference to each of the first and third embodiments a suitably shaped mandrel may be coated with an appropriate plastic and the inner coil formed by being wound over the plastic coating with the mandrel therein, or separately wound, partially unwound and thence allow to contract over the coating. Thence the formed outer coil is partially wound as described with reference to FIGS. 1–3, has the mandrel with the inner coil inserted thereinto and thereafter the outer coil is allowed to contract to form an interference fit with the inner coil and the mandrel is removed from within the plastic coating. Alternately in place of using a mandrel the cable may be formed first and then the interior of the cable spray coated with plastic. In either event, with the cable and inner tubular portion formed of appropriate axial lengths and fixing the cable proximal end to the fitting, the third embodiment of the catheter is formed.

To form the first embodiment the procedure may be the same as that set forth in the preceding paragraph other than before or after joining the cable to the appropriate fitting, the outer coil is plastic coated, for example by dipping, or spray coating, or positioning a heat shrinkable sleeve on the outer coil in surrounding relationship and a heat shrinking step carried out. To form the second embodiment of the catheter either before or after brazing the cable to the fitting the outer coil has a plastic coating formed thereon by one of the plastic coating steps set forth in the preceding sentence.

As to any of the embodiments of the catheter, instead of brazing the cable to the fitting, the cable together with tubular portions of the inner and/or outer tubular portions abutting thereagainst are joined to the fitting by a suitable epoxy or another compound, particularly if the fitting is made of a non-metallic material. The shape of the distal end portion of the fitting and the proximal end portion of the cable and the inner and/or outer tubular portions may be varied. As an example fitting portion 104 may of an outer diameter the same as the tubular portion 108 and have a short tubular extension joined to portion 104 to extend in surrounding relationship to at least part of portion 102 to form an annular recess into which the cable proximal end portion extends, and the tubular portion 108 shortened to have its proximal, annular terminal edge abut against the short tubular extension.

With reference to each of the embodiments of the catheters, the inner and outer coils are joined to one another only at their proximal and distal end portions and thus are not joined to one another throughout nearly their entire axial lengths, but merely in interference fitting relationship. The catheters provide a substantially 1:1 transfer of torque from the fitting to the distal end of the cable M, N incorporated in the catheter.

Preferably each coil of the cable of this invention in a linear cable relaxed condition, whether or not incorporated as part of another medical device, throughout substantially its entire axial length has adjacent helices in abutting relationship with the helices being of the same pitch (with the possible exception of portion 81a of FIG. 10).

The cable of this invention is of particular benefit for use in vascular vessels wherein it is desired to have a cable as part of medical apparatus that is of an outer cable diameter of about 1/16" or less. Advantageously the wires of the coils are of a diameter of about 0.001"–0.010" and as an example of this invention and not otherwise as a limitation thereon, the outer coil in its relaxed non-assembled condition an outer coil outer diameter Y of about 0.038" and an inner diameter X of about 0.028", and the inner coil N in its relaxed non-assembled condition an inner coil outer diameter Z of about 0.030". With coils of dimensions set forth in the preceding sentence there would be about a 0.002" interference fit. Cables of this invention may be of varying lengths, for example of any length of about up to 14', and advantageously an interference fit of about 0.002"–0.010", depending upon the particular use.

Each strand may, in cross section be round, ribbon shaped or other desired cross section. For medical uses, advantageously each strand of wire is made of a material able to have a spring temper, of a diameter of about 0.002–0.010", has a tensile strength of about 100,000–400,000 psi and preferably 150,000–400,000 psi and made of a metallic material suitable for use in a human body, for example stainless steel, MP-35, or other metals or metal alloys containing one or more of, for example, tungsten, platinum, cobalt, nickel or other precious metals.

Although each coil has been described as being made of four wires, it is to be understood each coil may be made of 2 or more metal wire strands. Further the cable has been described as being made of two coils. However the cable may be made of three or more coils in concentric relationship. For example there may be provided a third coil (shown in FIG. 31 at 0) that is multifilar and wound to, in a relaxed non-assemblied condition, have a coil inner peripheral diameter that is somewhat smaller than the outer peripheral diameter of the assembled inner and outer coils, for example about 0.002"–0.010". After the inner and outer coils M and N, respectively have been assembled, an unwinding force is applied to the third coil to radially expand it sufficiently that the assembled inner and outer coils can be inserted into the third coil; and after the inserting step, the unwinding force is removed to allow the third coil to contract to form an interference fit with the coil N. Now the cable is made up of three coils with the third coil being the outer coil, coil N the intermediate coil, and coil M the inner coil with coil N being wound in the opposite direction from that of the third coil and the inner coil M. It is to be understood that the strands of wire are cleaned before forming the third coil, that the third coil is cleaned before the insertion step and the assembled three coils are also cleaned.

What is claimed is:

1. A catheter comprising an axially elongated multifilar metal inner coil having convolutions in abutting relationship, a distal end portion, a proximal end portion and an inner peripheral wall portion, an axially elongated multifilar outer metal coil having convolutions in abutting relationship, a distal end portion, a proximal end portion and an outer peripheral wall portion, the outer coil throughout at least substantially its entire axial length in its relaxed condition being of a smaller inner diameter than the outer diameter of the inner coil in its relaxed condition and being in coaxial abutting relationship to the inner coil, first means for joining the proximal end portions of the coils to one another, second means for joining the distal end portions of the coils to one another in fixed relationship, and third means for forming a generally tubular resilient portion joined to at least one of the inner and outer coil peripheral wall portions to extend radially outwardly and radially inwardly relative to the respective one of the peripheral wall portions to which it is joined, said third means extending at least nearly the axial length of the coils, including axially more remote from the proximal end portions of the coils than the distal end portions of the coils, and having a distal outlet opening, the coils being helically wound in opposite directions.

2. The apparatus of claim 1 further characterized in that the third means is made of a plastic material and that there is provided a catheter luer fitting joined to the proximal end portions of the coils in fixed relationship therto, and that each coil in a linear relaxed condition has its adjacent helices in abutting relationship throughout its axial length.

\* \* \* \* \*